(12) United States Patent
Hirota et al.

(10) Patent No.: US 7,160,512 B2
(45) Date of Patent: Jan. 9, 2007

(54) METHOD FOR MANUFACTURING BIOCHIPS

(75) Inventors: Toshikazu Hirota, Kuwana (JP); Takao Ohnishi, Nishikasugai-gun (JP); Hiroyuki Tsuji, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 743 days.

(21) Appl. No.: 10/135,200

(22) Filed: Apr. 30, 2002

(65) Prior Publication Data

US 2003/0012698 A1 Jan. 16, 2003

(30) Foreign Application Priority Data

May 1, 2001 (JP) .............................. 2001-134719

(51) Int. Cl.
*B01L 3/02* (2006.01)
(52) U.S. Cl. ................. 422/100; 422/99; 422/101; 422/102; 422/64; 422/65; 436/180
(58) Field of Classification Search .......... 422/99–102, 422/64, 65; 436/180
See application file for complete search history.

(56) References Cited

U.S. PATENT DOCUMENTS

| | | | |
|---|---|---|---|
| 5,882,930 A | | 3/1999 | Baier |
| 5,958,342 A | | 9/1999 | Gamble et al. |
| 6,001,309 A | * | 12/1999 | Gamble et al. ............ 422/100 |
| 6,102,984 A | * | 8/2000 | Carl ..................... 73/864.24 |
| 6,232,072 B1 | | 5/2001 | Fisher |
| 6,814,937 B1 | | 11/2004 | Hirota et al. |
| 2001/0010916 A1 | | 8/2001 | Schleifer et al. |

FOREIGN PATENT DOCUMENTS

| | | |
|---|---|---|
| EP | 1 093 855 | 4/2001 |
| EP | 1 094 120 | 4/2001 |
| EP | 1 094 318 | 4/2001 |
| EP | 1 166 887 | 1/2002 |
| GB | 2 354 841 | 4/2001 |
| JP | 59-178258 | 10/1984 |
| JP | 3-101960 | 4/1991 |
| JP | 05-232124 | 9/1993 |
| JP | 06-040030 | 2/1994 |
| JP | 08-233710 | 9/1996 |
| JP | 2000-287670 | 10/2000 |
| JP | 2001-066305 | 3/2001 |
| JP | 2001-116750 | 4/2001 |
| JP | 2001-337096 | 12/2001 |

OTHER PUBLICATIONS

U.S. Appl. No. 09/302,898, filed Apr. 30, 1999, Webb et al.
U.S. Appl. No. 09/359,527, filed Jul. 22, 1999, Webb et al.
Patent Abstracts of Japan, Publication No. 2001-021558 (Jan. 26, 2001), Application No. 2000-126767 (Apr. 27, 2000) in the name of Agilent Technologies Inc.

* cited by examiner

*Primary Examiner*—Jill Warden
*Assistant Examiner*—Jyoti Nagpaul
(74) *Attorney, Agent, or Firm*—Burr & Brown

(57) ABSTRACT

A biochip manufacturing method can densely align spots of a plurality of samples in predetermined locations on a substrate using a discharge head equipped with one or more discharge modules composed of one or more discharge units, and a first moving table on which one or more trays with one or more substrates fixed thereon are detachably mounted. According to the biochip manufacturing method, the high precision in the operation for densely aligning and fixing droplets with a minute volume on a predetermined substrate (micro spot-forming operation) can be attained, and the time required for the micro spot-forming operation can be shortened as well.

21 Claims, 16 Drawing Sheets

METHOD FOR MANUFACTURING BIOCHIPS

BACKGROUND OF THE INVENTION AND THE RELATED ART

The present invention relates to a method of manufacturing biochips. More particularly, the present invention relates to a method of manufacturing biochips, such as a DNA microarray, which enables the operation of densely aligning and fixing droplets with a minute volume onto a predetermined substrate (micro spot-forming operation) to be performed with increased precision, thereby shortening the time required for the micro spot-forming operation.

Progress in methods for analyzing gene structures has been remarkable in recent years. A number of gene structures, including structures of human genes, have been identified. Biochips such as a DNA microarray in which micro spots containing several thousands to several tens of thousands different DNA fragments are arrayed on a substrate, such as a glass microscope slide, are used in the analysis of such gene structures.

A quill method, pin-and-ring method, and spring pin method have been widely used for forming micro spots in the preparation of DNA microarrays and the like. In all these methods it is necessary to suppress fluctuations in the volume and shape of the micro spots, to maintain a fixed distance between the micro spots, and to prevent contamination due to mutual invasion of the micro spots. In view of higher density requirements in the future, increased precision and speed in the micro spotting operation and improvement in the resulting product quality are desired.

In the quill method, a sample stored in a recess formed at the tip of a pin is transferred onto a substrate by causing the tip to come in contact with the substrate to form a micro spot. The pin tip may be deformed or damaged by contact with the substrate, causing a durability problem. Another problem is cross contamination due to incomplete washing of the sample stored in the recess.

In the pin-and-ring method, a sample solution in a microplate is reserved in a ring. A pin tip dispenses the solution so that the solution reserved goes through the inside of a ring and forms spots on a substrate. The number of kinds of samples capable of reserving in one operation depends on the number of rings. Because that number is conventionally several at most, in order to form several thousand to several tens of thousands kinds of micro spots, about several hundred to several thousand times of washing and drying operations are required. This method has a problem in the productivity.

The spring pin method is a method of producing micro spots on a substrate by transferring a sample attached to a pin tip by pressing the pin tip against the substrate. The device has a double pin structure enclosed in a spring to avoid damage to the pin and substrate when the sample is dispensed. This method, however, can basically spot only one spot per each reserving. Thus, this method also have a problem in the productivity.

To improve productivity, a method of placing a large number of substrates of several tens of sheets on a manufacturing apparatus at one time and forming micro spots may be a possible idea. This method, however, requires a large-scale manufacturing facility and involves a high cost. Even if biochips are manufactured using a large unit, the time required for processing one sheet of substrate (i.e. the time for discharging a sample on one substrate and forming spots) is increased, resulting in a lengthened period of time for completing the process for all substrates. Therefore, the sample used at the initial spotting operation and that at the final spotting operation may not be the same due to denaturing, and this causes a problem that the quality of the resultant biochip is deteriorated. The problem is particularly serious in the case of biological substances which are easily denatured.

In another method for manufacturing a large number of substrates of several tens of sheets, a plurality of units are used to perform the above-described spotting operation side by side at the same time. This method not only involves a high equipment cost, but also requires samples for spotting to a number of units, posing a problem when the sample is a biological substance which is precious and available only in a small amount. Such a method, even if materialized, brings about another problem of fluctuation in the quality each time spotting rods are replaced for a number of units.

Spotting with the application of an ink jet method used in ink jet printers has also been studied. For example, there is disclosed that an ink-jet recording head, in which the ink-discharge nozzle hole is designed to have at least one corner to provide a capillary force (JP-A-59-178258).

There is disclosed an ink jet head in which the sample discharge port has a symmetrical 2n-polygon (n=3 or more) and the cross-section of the ink flow path in the direction vertical to the ink discharge direction has a trapezoidal configuration (JP-A-3-101960).

The manufacturing method using such an ink-jet system excels in an increased speed of spotting operation and uniform spotting product quality.

In the manufacturing method using such an ink-jet system, however, samples are sent to discharge heads to discharge micro liquid spots directly from the outside via a thin tube connected to the head. Because some samples may adhere to the wall of this thin tube, the amount of samples required increases as the volume of the tube increases. Thus, the precious sample is unavoidably wasted.

In addition, a longer time is required for thoroughly washing the tube when discharge heads are washed before charging different samples.

Furthermore, a longer time is required for removing the discharge heads from the unit because of the connected tube. Since frequent removal of once installed discharge heads is impractical, operations for washing the discharge heads and charging and discharging the samples are carried out with the discharge heads installed. Therefore, the washing operation involves a number of physical restrictions, resulting in insufficient washing.

Moreover, confirmation of discharging is difficult because discharging must be confirmed with the discharge heads as installed on the unit. If any discharge head malfunctions, discharging of that part of the unit must be suspended. Otherwise, it is impossible to operate the unit and start the spotting operation until the time when the discharging is restored and normal discharging can be completely confirmed.

If the unit is restarted without complete confirmation of normal discharging or if discharging operation is continued with bubbles and the like lingering in the tube, discharging becomes unstable while the spotting operation is continued on a number of substrates. Some substrates may have spots dropped on deviated points or may not have required spots on proper points, resulting in impaired quality of biochips.

For example, many biological samples containing a DNA and the like have a high viscosity. These samples are required to be rapidly dried upon discharge and attachment to a substrate before spots expand on the substrate. These samples tend to dry or increase the viscosity at a nozzle tip. The nozzle tip may become choked and cannot discharge the sample.

The present invention has been achieved in view of the above problems and has an object of providing a method of manufacturing biochips such as a DNA microarray which enables an operation of densely aligning and fixing droplets with a minute volume on a predetermined substrate (micro spot-forming operation) to be performed with increased precision, thereby shortening the time required for the micro spot-forming operation.

SUMMARY OF THE INVENTION

To accomplish the above object, the present invention provides a method for manufacturing a biochip with spots of plural kinds of samples densely aligned on a substrate, wherein a sample containing a reagent specifically reactive with a specimen and providing information relating to the structure and functions of the specimen is introduced into a cavity via a sample charge port of a discharge unit having a sample charge port, a cavity, and a sample discharge port formed thereon, a substrate is provided at the position facing to the sample discharge port, the sample having been introduced into the cavity is discharged onto the substrate from the sample discharge port as droplets with a very small volume, thereby forming spots on the substrate, and the process is repeated for a plural kinds of the above-mentioned samples; said biochip manufacturing method is characterized by providing a discharge head equipped with one or more discharge modules each of which being formed from one or more discharge units, introducing at least one of said plural kinds of samples into a cavity from a sample charge port of the discharge unit in a discharge head, so that one discharge unit is provided with only one kind of sample, transferring a first moving table, on which one or more trays with one or more substrates fixed thereon are detachably mounted, to a sample discharge point of the discharge unit corresponding to a predetermined point on the substrate, and discharging the sample having been introduced into the cavity from the sample discharge port to a predetermined point on the substrate as liquid droplets, thereby spots of plural kinds of samples are densely aligned on the substrate.

In the biochip manufacturing method of the present invention, it is preferable to provide the first moving table on which the tray being placed and a second moving table on which the discharge head being detachably mounted, and adjust the relative position of the substrate and the sample discharge port.

In the above method, it is preferable that each of said plural kinds of samples is individually introduced into the cavity by charging it from the charging port of the corresponding discharge unit, and one of the samples introduced into the cavity is discharged as liquid droplets onto a predetermined point on the substrate, thereby forming spots on the substrate, and this process is repeated for the plural kinds of samples.

Further, it is preferable that at least one sample among said plural kinds of samples is introduced into the cavity by charging it from the charging port of the discharge unit of the discharge head so that only one kind of sample is provided to one discharge module, and said one sample introduced into the cavity is discharged as liquid droplets onto a predetermined point on the substrate, thereby forming spots on the substrate, and this process is repeated for the above plural kinds of samples.

In the above-mentioned biochip manufacturing method, it is preferable that two or more discharge heads are provided, at least one sample among said plural kinds of samples is introduced into the cavity by charging it from the sample charge port of each discharge unit of each discharge head, one discharge head into which the sample has been introduced is mounted on the second moving table, the sample having been introduced into the cavity is discharged onto the predetermined point on the substrate as liquid drops, with adjusting the relative position of the substrate and the sample discharge port of said one discharge head, thereby forming spots of the sample on one substrate, then, said one discharge head is removed from the second moving table and another discharge head into which a sample different from said sample has been introduced is mounted on the second moving table, and this different sample having been introduced into the cavity is discharged onto the predetermined point on the substrate as liquid drops, with adjusting the relative position of the substrate and the sample discharge port of said one discharge head, thereby forming spots of the sample on one substrate, and the process is repeated a plural number of times equal to the number of discharge heads.

In a preferred embodiment of the above biochip manufacturing method, a plural number of trays is used, one tray among the plural number of trays is mounted on the first moving table, and the sample having been introduced into the cavity is discharged onto the predetermined point on the substrate as liquid drops, with adjusting the relative position of the substrate fixed to said one tray and the sample discharge port, thereby forming spots of the sample on said one substrate, then, said one tray is removed from the first moving table and another tray to which the other substrate is fixed is mounted on the first moving table, and each sample having been introduced into the cavity is discharged onto the predetermined point on the substrate as liquid drops, with adjusting the relative position of the other substrate and the sample discharge port, thereby forming spots of the sample on one substrate, and the process is repeated a number of times equal to the number of the trays.

In another preferred embodiment of the above biochip manufacturing method, plural number of robots each of which is composed of said first moving table and second moving table is provided, said tray on which the substrate is fixed is mounted on the first moving table forming one robot among said plural number of robots, the sample provided to one discharge head mounted on said second moving table is discharged onto the predetermined point on the substrate as liquid drops, with adjusting the relative positions of the substrate and the sample discharge port, thereby forming spots of the sample provided to one discharge head on the substrate, then, said one tray is removed and the removed tray is mounted on one first moving table forming other robot among said plural number of robots, the sample provided to the other discharge head on the one second moving table composing said other robot is discharged onto the predetermined point on the substrate as liquid drops, thereby forming spots of the sample on one substrate, and the process is repeated a number of times equal to the number of the robots.

In the above preferred embodiment, spots are formed on another substrate with said one robot using another tray on which said another substrate is fixed, during a period that spots are formed on said one substrate by using said another robot after forming spots on said one substrate using said one robot.

In a further preferred embodiment of the above biochip manufacturing method, at least one of two operations is carried out, wherein one operation is measuring the position of said discharge head with respect to the absolute coordinates of said second moving table, which is performed each time the discharge head is mounted on the second moving table, and another operation is measuring the position of said tray with respect to the absolute coordinates of said first moving table, which is performed each time the tray is mounted on the fist moving table, and the relative positional relationship of the discharge head, the tray is calculated based on the measured results, and the sample is discharged onto the predetermined point on the substrate fixed on the tray to form spots.

In the above preferred embodiment, the positional deviation of the discharge head and the tray is corrected by repeating the position measurement of the discharge head with respect to the absolute coordinates of the second moving table and the position measurement of the tray with respect to the absolute coordinates of the first moving table for an optional number of times.

In the above preferred embodiment, the discharge head is provided with head reference marks at two or more predetermined locations, the second moving table is provided with second table fixing references at two or more locations of the immovable part thereof, the relative positions of the head reference marks and the second table fixing references are measured at two or more locations, and based on the measured results obtained, the direction and amount of deviation of the mounting position of the head are corrected by decomposing the deviation in the longitudinal, lateral, and rotational directions.

In the above embodiment, it is preferable that the first moving table is provided with the table reference marks at two or more locations on the movable part thereof and first table fixing reference marks at two or more locations on the immovable part thereof, the relative positions of the head reference mark and the first table fixing references are measured at two or more locations, the relative positions of the tray reference marks, provided at two or more predetermined locations of the tray, and the first table fixing references are measured at two or more locations, and based on the measured results obtained, the direction and amount of deviation of the mounting position of the tray are corrected by decomposing the deviation in the longitudinal and lateral directions.

In the method of the present invention, at least one of the first moving table and the second moving table is moved while correcting by using an outside reference fixed in the immovable part of at least one of the first moving table and the second moving table.

In the above case, said outside reference is made from a material with a low thermal expansion coefficient.

In a still further preferred embodiment of the present invention, the first moving table and the second moving table are moved while adjusting the relative position of the substrate and the sample discharge port so that the discharge head and the tray are brought to predetermined positions, and then the sample is discharged from the sample discharge port to form spots in the state in which the discharge head and the tray are in stationary conditions.

In a still further preferred embodiment, discharge head equipped with two or more discharge modules and a tray equipped with two or more substrates fixed thereon are provided, the tray is moved to have a predetermined positional relationship between the sample discharge ports of all discharge units in one discharge module and one substrate among the two or more substrates fixed on the tray, while the relative positions of the sample discharge ports for all discharge units in one discharge module and one substrate among the two or more substrates fixed on the tray are simultaneously adjusted, the sample having been stored in said one discharge module onto said one substrate is discharged from the sample discharge ports for all discharge units in said one discharge module, thereby forming spots corresponding to the sample discharge ports for all discharge units in said one discharge module, and, the tray is moved to establish a predetermined positional relationship between said one substrate and the sample discharge ports of all discharge units in another discharge module, while the relative positional relationship between the substrate and the sample discharge ports of all discharge units in said another discharge module are simultaneously adjusted, the sample stored in said another discharge module is discharged onto said one substrate from the sample discharge ports for all discharge units in said another discharge module, thereby spots corresponding to the sample discharge ports for all discharge units in said another discharge module are formed; this process being repeated for a number of times equal to the number of discharge modules arranged in said discharge head, thereby spots on said one substrate corresponding to discharge ports for all discharge units present in the discharge head is formed, and the tray is moved to secure another substrate on the tray, thereby spots corresponding to sample discharge ports for all discharge units present in the discharge head are formed; this process being repeated for a number of times equal to the number of substrates fixed on the tray, with maintaining intervals of sample discharge operations from said discharge units in said two or more discharge modules almost the same.

In the above preferred embodiment, it is preferred that the sample having been stored in said one discharge module is discharged onto said one substrate from the sample discharge ports for all discharge units in said one discharge module, thereby spots being formed; then the tray is moved with the discharge head being in stationary conditions to establish a predetermined positional relationship between one substrate and the sample discharge ports of all discharge units in another discharge module, while the relative positional relationship between the substrate and the sample discharge ports of all discharge units in said another discharge module are simultaneously adjusted, and, after spots are formed on said one substrate corresponding to sample discharge ports for all discharge units present in the discharge head, when the tray is moved with the discharge head being in stationary conditions to establish a predetermined positional relationship between said another substrate and said sample discharge ports of all other discharge units in said another discharge module, while the relative positional relationship between the substrate and the sample discharge ports of all discharge units in said another discharge module are adjusted.

It is further preferable to vertically remove the discharge head from the tray before moving the tray, and after moving the tray, to move the discharge head to vertically approach the tray.

In the above embodiment, the sample is preferably discharged from the discharge units at regular intervals merely for the purpose of dummy discharge during the time other than the period in which a series of operations for forming spots on predetermined points on substrates by discharging samples from the sample discharge ports are performed.

In this instance, the intervals of the dummy discharge are preferably almost the same as the intervals of the sample discharge, beginning from before the time when the series of operations is started for forming spots on predetermined points on substrates by discharging samples from the sample discharge ports.

It is further preferable that the upper surface of the substrate is irradiated with a coaxial light after forming spots on predetermined points of the substrate by discharging the samples from said sample discharge ports, and a spot configuration is measured by the image produced by reflection of light on the surface of the substrate on which spots have been formed, thereby accumulating propriety information about the spots.

BRIEF DESCRIPTION OF THE DRAWINGS

FIGS. 2(a) and 2(b) are schematic views for illustrating a discharge unit forming a biochip-manufacturing apparatus used in one embodiment of the biochip manufacturing method of the present invention, wherein FIG. 2(a) is a sectional view of the entire unit and FIG. 2(b) is a detailed illustration of FIG. 2(a).

FIGS. 3(a) and 3(b) are views for illustrating discharge heads forming a biochip-manufacturing apparatus used in one embodiment of the biochip manufacturing method of the present invention, wherein FIG. 3(a) is a plan view seen from the bottom and FIG. 3(b) is a plan view seen from the side.

DESCRIPTION OF PREFERRED EMBODIMENT OF THE INVENTION

Embodiments of the biochip manufacturing method of the present invention will now be specifically explained hereinafter with reference to the drawings. The present invention should not be construed to be limited by these embodiments. Various alterations, modifications, and improvements are possible within the scope of the present invention based on the knowledge of those who skilled in the art.

Figure 1:
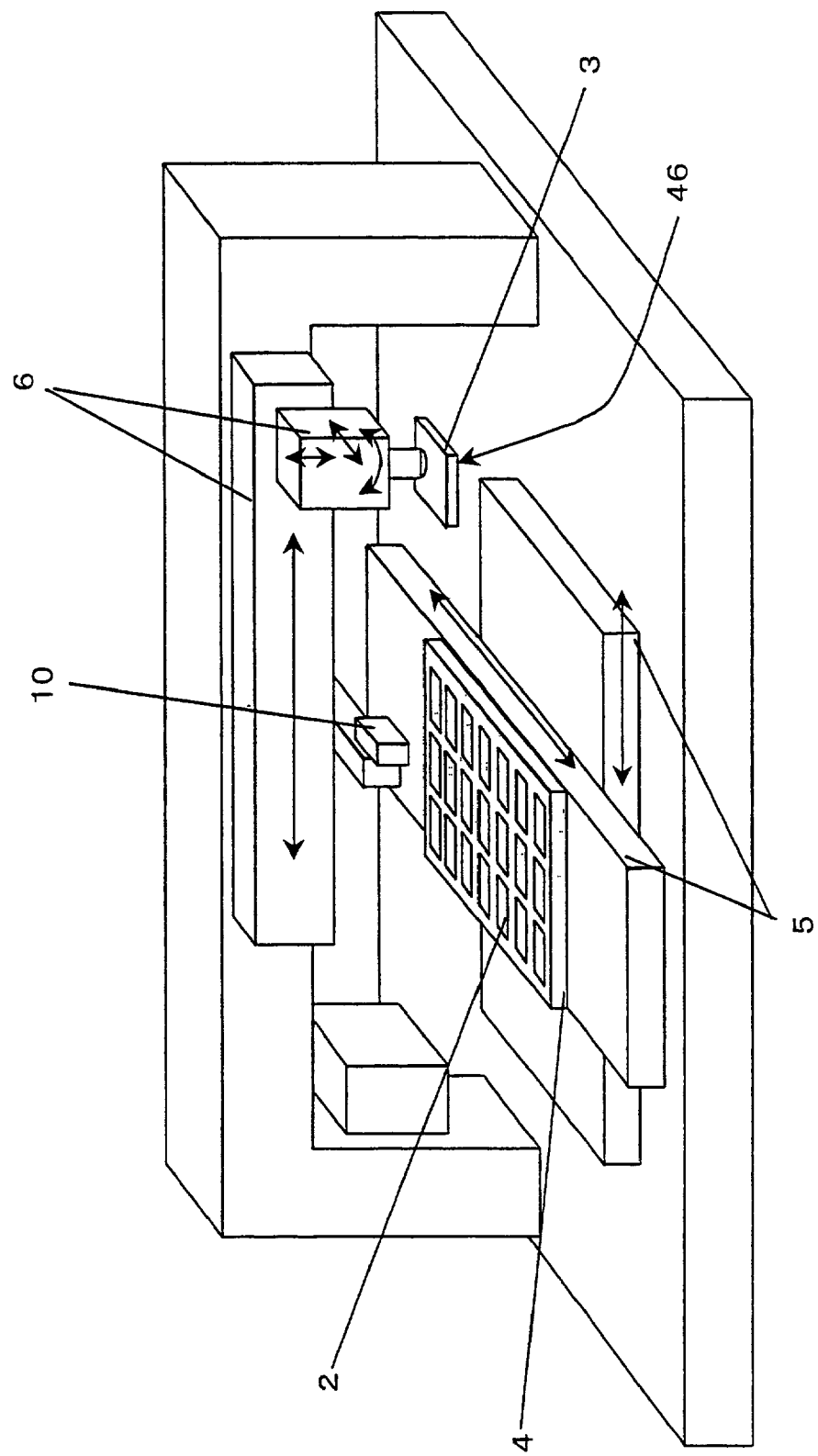
FIG. 1 is a perspective view showing a configuration of a biochip-manufacturing apparatus used in one embodiment of the biochip manufacturing method of the present invention.

In one embodiment of the present invention, biochips are manufactured using a biochip-manufacturing apparatus 1 as shown in FIG. 1. In the biochip manufacturing method of the present embodiment, a sample containing a chemical agent specifically reacting with a specimen and providing information relating to the structure and functions of the specimen is introduced into a cavity 43 via a sample charge port 42 of a discharge unit having a sample charge port 42, a cavity 43, and a sample discharge port 46 formed therein, as shown in FIG. 2(a); a substrate 2 such as a microscope glass slide is provided at the position facing to the sample discharge port 46, as shown in FIG. 1, and the sample introduced into the cavity 43 (see FIGS. 2(a), 2(b)) is discharged onto a substrate 2 from the sample discharge port as droplets with a very small volume, thereby forming spots on the substrates 2; this process is repeated for a plurality of samples to manufacture a biochip with a plural types of spots formed from a plural types of samples being densely aligned on the substrate 2; wherein, as shown in FIGS. 3(a), 3(b), at least one of said plurality of samples is introduced into the cavity using a discharge head 3 provided with discharge modules 7, each formed from one or more discharge units 8, from the sample charge port of the discharge unit in the discharge head 3, so that one discharge unit 8 is provided with only one type of sample; further wherein, as shown in FIG. 1, the first moving table 1, on which one or more trays 4 with one or more substrates 2 fixed thereon are detachably mounted, is moved to a sample discharge point of the discharge unit 8 (see FIG. 3(a)) corresponding to the predetermined point on the substrate 2; wherein samples introduced into the cavity are discharged from the sample discharge port to the predetermined point on the substrate 2 as liquid droplets, thereby causing spots from a plurality of samples to be densely aligned on the substrate 2.

As mentioned above, since the discharge head 3, the tray 4, and the first moving table 5 are separately arranged and adjusted before supplying of the sample to the substrate 2 (spotting), introducing of a sample into the discharge head 3, confirmation of discharge, correction of defective discharge points, the manner of fixing the substrate 2 to the tray 4, the timing of fixing, storage of the substrate 2, and the like are carried out under optimal conditions separately from the first moving table 5. The method ensures improvement in the shape, spot position precision, and uniformity of spots formed on the substrate 2, making it possible to increase sensitivity of the resulting biochips and reduce quality dispersion.

Figure 2A:
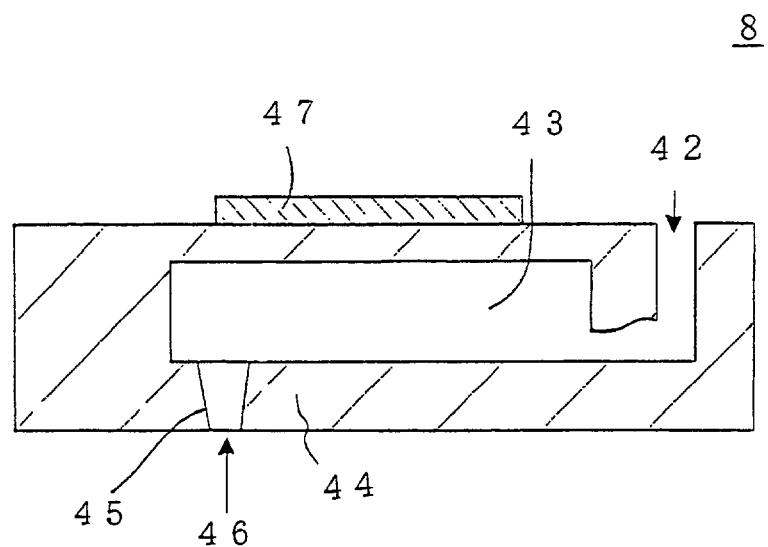
Figure 3A:
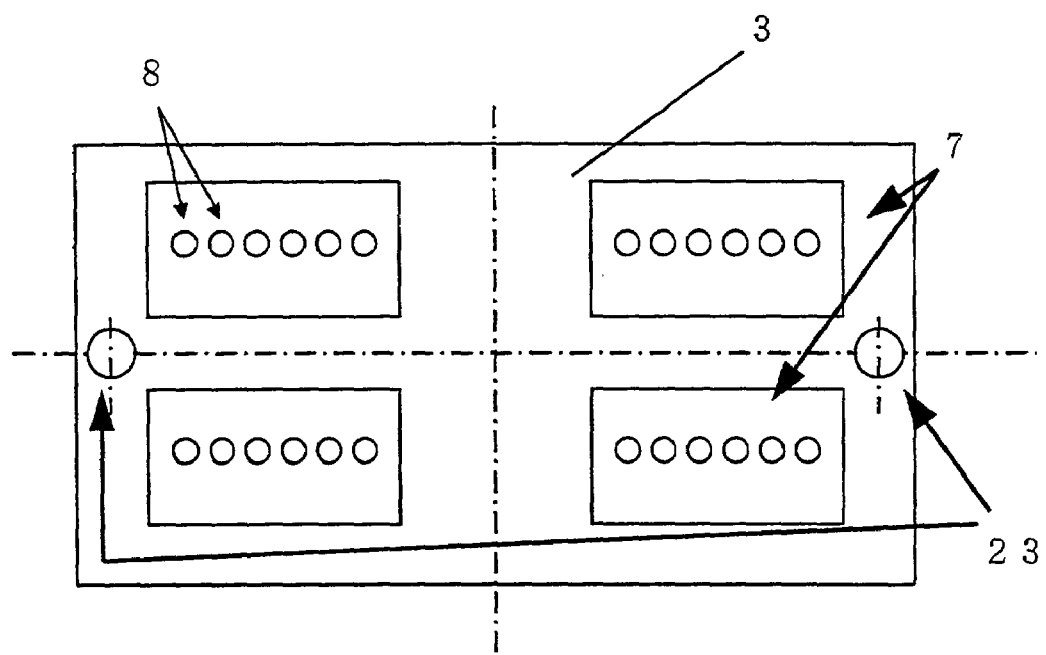
Figure 3B:
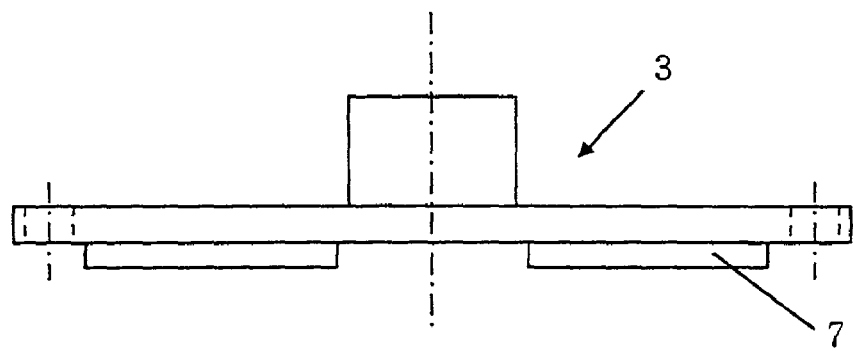

As shown in FIG. 2(a), an embodiment of the present invention has a sample charge port 42 for charging a sample from outside the discharge unit 8, a cavity 43 for receiving and temporarily storing the sample, and a sample discharge port 46 for discharging the stored sample through a through-hole 45 in a nozzle section 44. The main body of the discharge unit 8 is provided with a piezoelectric/electrostrictive element 47 on the external surface thereof in a location corresponding to the location of cavity 43. Driving the piezoelectric/electrostrictive element 47 can vary the volume of the cavity 43, whereby a specific amount of the sample stored in the cavity 43 is discharged from the sample discharge port 46. The discharge unit main body 8 thus formed is preferably used.

Figure 2B:
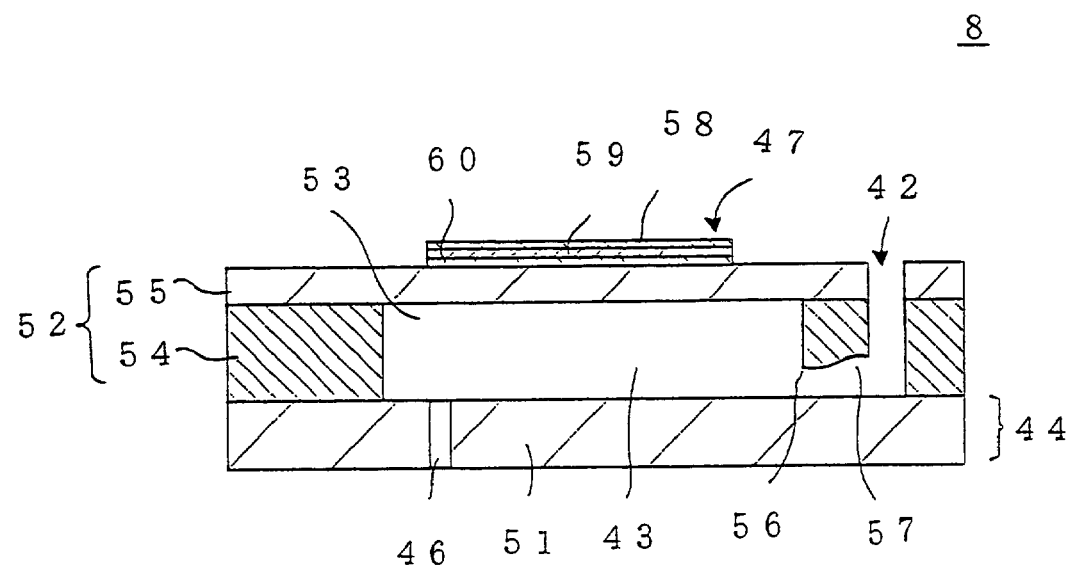

Specifically, as shown in FIGS. 2(a), 2(b), the nozzle section 44 may be formed from a nozzle plate 51 in the form of a thin plate made of PET resin, through which a sample discharge port 46 comprising of one or more through-holes 45 is provided. The nozzle section 44 (through-hole 45) can usually be formed by a mechanical process such as die punching or the like. When a resin such as PET, polyimide, or the like is used as the material for the nozzle section, laser beam machining using an excimer laser or YAG laser of a high (3 or more) dimension is preferably used. For forming a cross-section configuration in the direction vertical to the axial direction of the through-holes 45, a beam scanning technique in which laser beams are caused to move along the cross-section configuration or a masking technique using a mask with a shape similar to the shape of the cross-section to be installed on the laser beam irradiation axis can be used. A masking technique which permits formation of a number of through-holes at the same time is preferred. On the other hand, a pump section 52 being composed of a spacer plate 54 in which one or more windows 53 are formed and a blockade plate 55 layered on one side of the spacer plate 54 for covering the window 53; all of them being formed from a green sheet of zirconia ceramic, and being laminated and sintered to form a discharge unit 8. The sample charge port 42 is provided in the blockade plate 55 and connected to an introduction hole 56 and a passage 57, both connected to the window 53 formed in a spacer plate 54. A piezoelectric/electrostrictive element 47 comprising a lower electrode 60, a piezoelectric/electrostrictive film 59, and an upper electrode 58 are formed on the external surface of the blockade plate 55.

Using the discharge unit 8 of this structure, the piezoelectric/electrostrictive element 47 is deformed when an electric field is formed between the upper electrode 58 and the lower electrode 60. This decreases the volume of the cavity (a pressure chamber) 43 formed by covering the window 53, whereby a sample (a fluid containing DNA fragments and the like) filled into the cavity 43 is discharged at a predetermined rate from the sample discharge port 46 connected with the cavity 43, allowing a biochip comprising micro spots to be aligned on a substrate. The structure of an ink jet device similar to the type shown in FIGS. 2(a) and 2(b) is described in JP-A-6-40030, for example.

In addition, any malfunctioning discharge unit 8 and discharge modules 7 may be replaced easily by composing the discharge head 3 with one or more discharge modules 7, and the discharge module 7 with one or more discharge units 8 as well, as shown in FIG. 3(a). In FIG. 3(a), the discharge module 7 is composed of six discharge units 8 and the discharge head 3 is composed of four discharge modules 7. The present invention is not limited to this embodiment and it may have any number of discharge modules 7 and discharge units 8.

Figure 4:
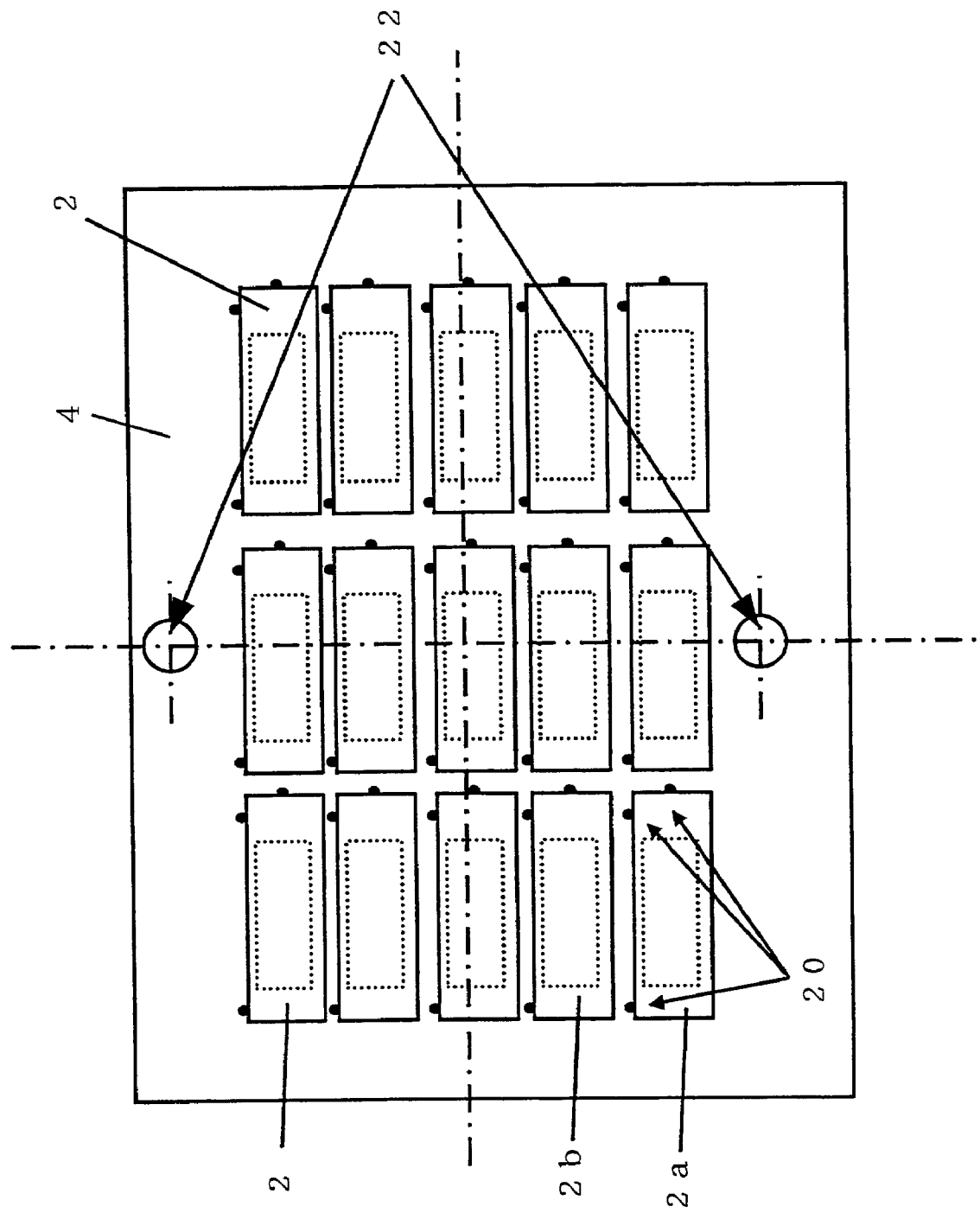
FIG. 4 is a plan view of a tray forming a biochip-manufacturing apparatus used in one embodiment of the biochip manufacturing method of the present invention seen from the top.

Furthermore, because the substrates 2 are fixed to the tray 4 using three substrate positioning pins 20, as shown in FIG. 4, precise securing can be ensured without putting unnecessary loads on the substrate and without deviation of the securing positions even if such a securing operation is repeated. Although a tray 4 being composed to have 15 sheets of substrates 2 fixed thereon, as is shown in FIG. 4, the present invention is not limited to this embodiment. There are no limitations to the number of substrates fixed on the tray 4.

Figure 5A:
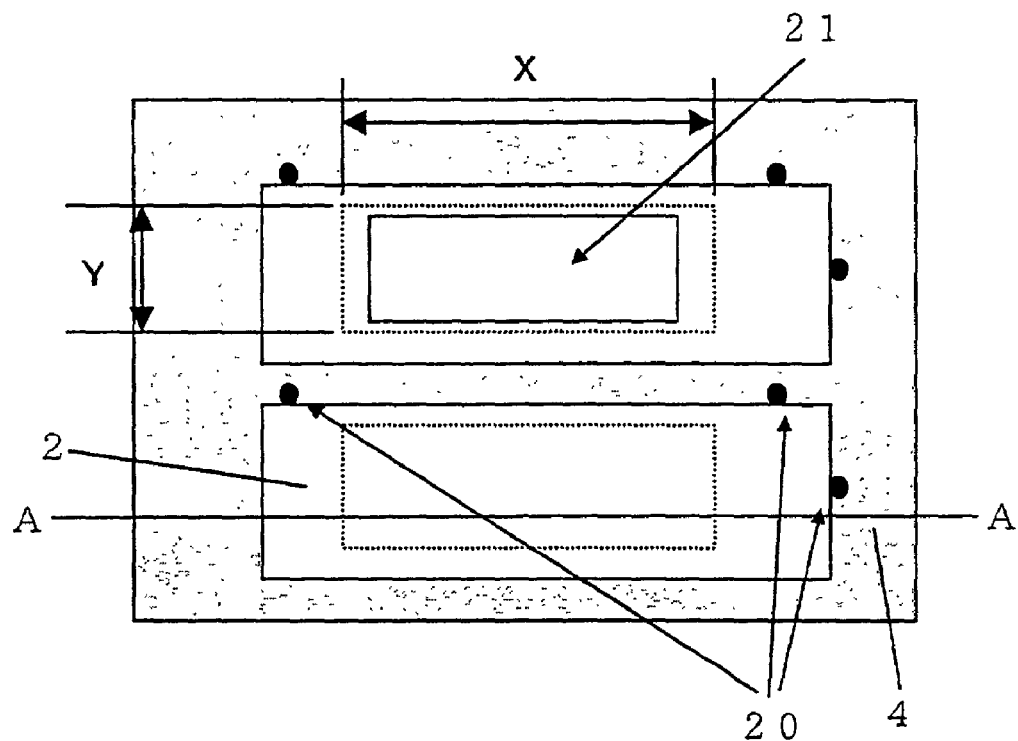
FIG. 5(a) is an enlarged plan view of part of the tray shown in FIG. 4
Figure 5B:
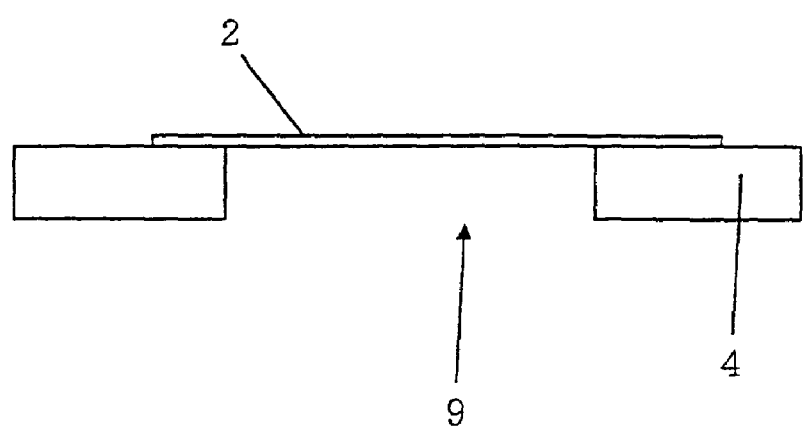
FIG. 5(b) shows a cross-section along the line A—A of FIG. 5(a).

In addition, not only the reduction in the weight of the tray 4 may be attained, but also the observation of spots may become easier as explained later by composing the tray 4 so as to have, as shown in FIGS. 5(a), 5(b), an opening 9 corresponding to the spotting area 21 on the substrate 2 fixed on the tray 4 onto which liquid drops are discharged. FIG. 5(b) shows a cross-section along the line A—A in FIG. 5(a).

Furthermore, because the detachable tray 4 with one or more substrates 2 fixed thereon is placed on the first moving table 5, the tray 4 can be installed on or removed from the biochip-manufacturing apparatus 1 without causing any parts to come directly into contact with the substrates 2, whereby contamination of the substrates 2 can be effectively prevented. Furthermore, a substrate height sensor 10 may be disposed on the first moving, table 5. By composing so, one may make the distance between the sample discharge port of the discharge head and the spotting surface of the substrate 2 constant, may make the speed of liquid drops reaching the surface of the substrate 2 constant, and may suppress fluctuation in the spotting area (diameter) without being influenced by the fluctuation of the thickness of the substrate 2. Thus, the spot quality is stabilized. In addition, any operational errors occurring at the time when the substrate 2 is fixed to the tray 4 may be prevented, and thus, the production yield of the biochips may be increased.

In the method of manufacturing of the biochip of this embodiment, as shown in FIG. 1, the relative positions of the substrate 2 and the sample discharge port can be adjusted by using the first moving table 5 on which the tray 4 is placed and the second moving table 6 on which the discharge head 3 is detachably mounted.

By composing so, it is possible to reduce the actual operating period of spotting to the lowest level by mounting the discharge head 3 onto the second moving table 6 after confirming that the sample droplets can be discharged without fail with introducing each sample to the discharge head 3, and providing a plurality of substrates 2 on the tray 4 and installing the tray 4 on the first moving table 5. This is effective in the case where the properties of the spotting sample rapidly change over time from the start of the discharge operation due to be exposed to the atmosphere, for example, when the sample contains an organic solvent which easily evaporates or an aqueous solution containing an organic polymer which readily increases in viscosity and rapidly dries, or in the case where the surface conditions of the substrate rapidly change due to moisture in the atmosphere, for example, when a polylysine coating substrate is used.

Even a small amount of samples can be spotted onto the substrates because it is unnecessary to use a thin tube for charging the sample to the discharge head 3 as in the case of a conventional ink jet method. Therefore, this embodiment is suitable as a method for manufacturing biochips for handling precious biological samples. Because the route to the point of sample discharge can be shorten, then clogging of the fluid path due to bubbles and the like can be prevented, it is possible to discharge liquid drops constantly from the discharge head 3 for a long time.

In addition, spots comprising several different types of samples can be easily aligned on the substrate 2 at a high density by changing the types of samples sent to each discharge unit 8 of the discharge head 3 (see FIG. 3(*a*)).

For instance, spots of several different types of samples can be easily formed on the substrate 2 in a short period of time by composing to form spots on the substrate 2 by individually introducing each of the several different types of samples into cavities by charging it from the charging port of the corresponding discharge unit 8 (see FIG. 3(*a*)) and discharging one of the samples introduced into the cavity as liquid droplets onto a predetermined point on a substrate 2, and repeat this operation for the several different types of samples as well.

Alternatively, one may compose to form spots on the substrates by introducing at least one sample among the several different types of samples from the charging port of each discharge unit 8 of the discharge head 3 (see FIG. 3(*a*)) so that only one type of sample may be provided to one discharge module 7 (see FIG. 3(*a*)) and causing this one sample introduced into the cavity to be discharged as liquid droplets onto a predetermined point on a substrate 2, and repeat this operation for several different types of samples as well. By doing so, one may improve the spot-forming speed, that is, the biochip production speed since one kind of samples is discharged at same time from a plurality of discharge units 8 possessed by one discharge module 7 to form a plurality of spots at once. This feature is particularly effective for the manufacture of a plurality of biochips first by forming a plurality of identical spot patterns on one sheet of glass slide or the like, and then dividing the glass slide or the like. Since a plurality of discharge units 8 possessed by one discharge module 7 must discharge an equal amount of sample at the same time, such discharge units can be suitably applied to an apparatus in which the discharge conditions for each discharge unit can be conveniently adjusted as in the case of the ink jet form in the present embodiment.

Alternatively, the biochip-manufacturing apparatus may comprise a plurality of discharge heads 3, wherein at least one type of sample among a plurality of samples is introduced into the cavity by being charged from the sample charge port of each discharge unit 8 (see FIG. 3(*a*)) of each discharge head 3, one discharge head 3 into which the sample has been introduced is mounted on the second moving table 6, the sample introduced into the cavity is discharged onto a predetermined point on the substrate 2 as liquid drops, while adjusting the relative positions of the substrate 2 and the sample discharge port of said one discharge head 3, thereby forming spots of the above-described sample on the substrate 2, then, said one discharge head 3 is removed from the second moving table 6 and another discharge head (not shown), in which a sample of a type different from the above-mentioned sample has been introduced, is mounted on the second moving table 6, the different type of sample introduced into the cavity is charged onto predetermined points on the substrate 2 as liquid drops, while adjusting the relative positions of the substrate 2 and the sample discharge port in a manner different from that applied to the discharge head 3, thereby forming spots of that different type of sample on the substrate 2, and the process is repeated a number of times equal to the number of the discharge heads.

By composing so, it is effective in the case where there are too many samples to be discharged onto the substrates 2 for one discharge head 3 to handle. Since it is possible to adjust the filling methods and discharge conditions in the actual discharge operations (such as a method of driving electric voltage) for each discharge head, a plurality of samples with different liquid properties can be uniformly spotted. In addition, the spotting operation while having several discharge heads previously filled with samples waiting to be mounted on the second moving table 6 in turn can reduce the operating period for spotting a plurality of different samples to the minimum.

In one modification of this embodiment, a plurality of trays 4 are used and one tray 4 among the plurality of trays 4 is mounted on the first moving table 5, the sample introduced into the cavity is discharged onto predetermined points on the substrate 2 as liquid drops, while adjusting the relative positions of the substrate 2 fixed on that tray 4 and the sample discharge port, thereby forming spots of the sample provided to the discharge head 3 on one substrate 2, then, that tray 4 is removed from the first moving table 5 and another tray (not shown) on which another substrate (not shown) is fixed is mounted on the first moving table 5, the sample introduced into the cavity is discharged onto predetermined points on another substrate (not shown) as liquid drops, while adjusting the relative positions of said other substrate (not shown) and the sample discharge port, thereby forming spots of the sample provided to the discharge head 3 on that another substrate (not shown), and the process is repeated a number of times equal to the number of the trays.

By doing so, one may increase the number of substrates to be able to process until the sample introduced into the cavity is entirely consumed. In addition, since a tray 4 on which one or more substrates 2 are fixed is mounted on the first moving table 5, the substrates 2 need not be directly contacted when installing or removing the tray 4, which not only prevents the substrates 2 from being contaminated, but also from being damaged even if the tray 4 is installed and removed a number of times. This is effective for processing a large amount of biochips. Also, the necessity of having a large biochip-manufacturing apparatus 1 can be avoided.

If one combine the composition of providing a plurality of discharge heads and the composition of providing a plurality of trays, the kinds of samples and the number of substrates may be increased independently, enabling both a large item small-scale production and a mass production.

Figure 8:
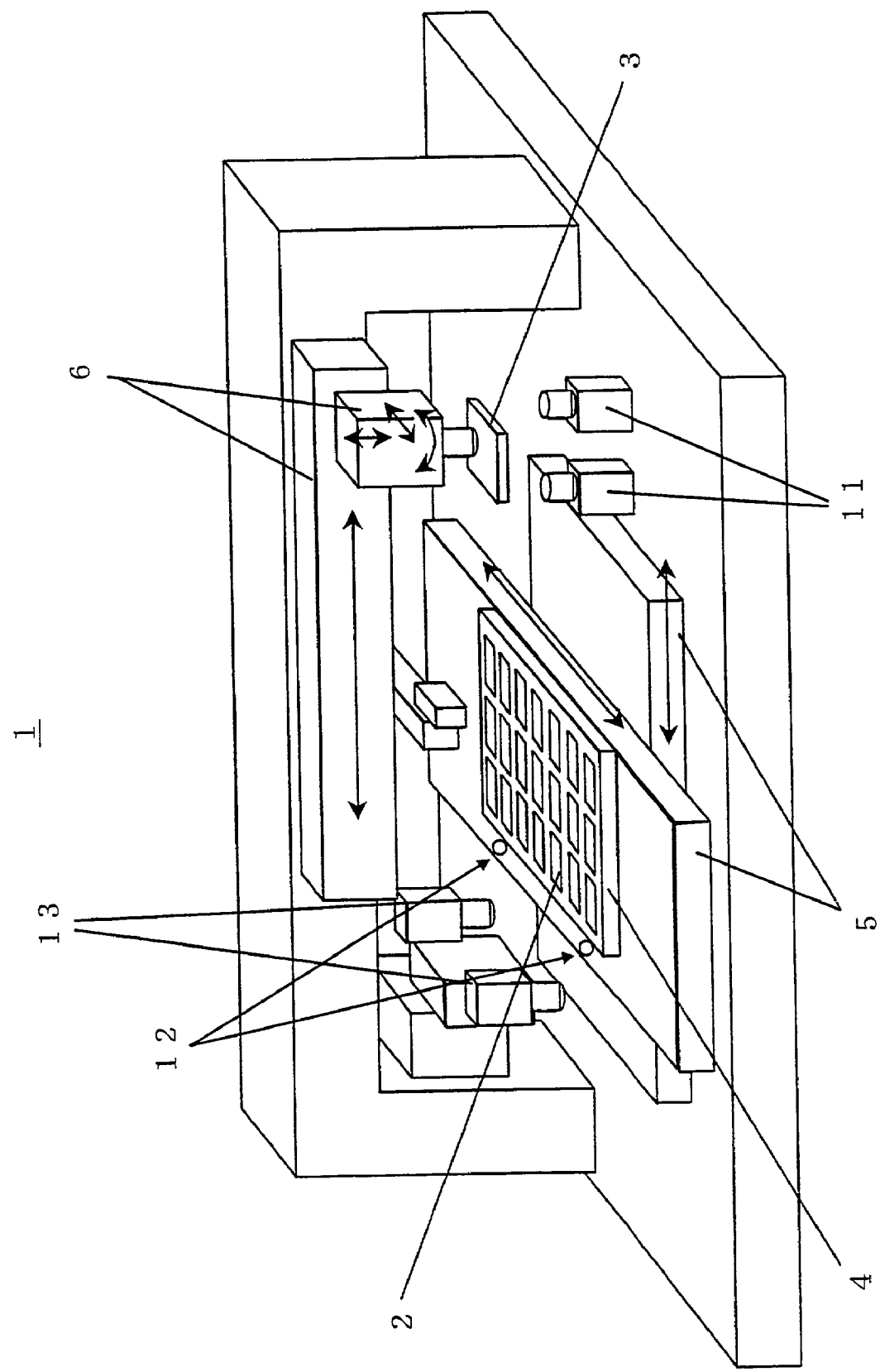
FIG. 8 is a perspective view showing a configuration of a biochip-manufacturing apparatus used in another embodiment of the biochip manufacturing method of the present invention.

This may be realized by, for example, using the biochip-manufacturing apparatus 1 shown in FIG. 8 with employment of a plurality of discharge heads 3 formed from a plurality of discharge units 8 as shown in FIG. 3(*a*), and a plurality of trays 4 on which a plurality of substrates 2 is fixed as shown in FIG. 4.

A sample containing necessary DNA fragments and the like is discharged onto a substrate 2 held on one tray 4, then the substrate 2 as well as the tray 4 is removed from the first moving table 5 of the biochip-manufacturing apparatus 1 and another tray on which a substrate with no spotted sample is fixed thereon is mounted on the first moving table 5 to cause the sample to be discharged. This operation is repeated for the number of trays meeting the required number of substrates. In this instance, a tray reference mark 22 (see FIG. 4), which is a light emitting device, is provided by forming a hole in two positions for each tray. The tray mounting position can then be confirmed and adjusted by observing and confirming these marks using a first table fixing reference 13 (see FIG. 8), such as a CCD camera, above the tray. Then, the discharge head 3 is removed from the second moving table 6 and another discharge head (not shown) containing another kind of DNA fragments or the like is mounted, then the spotting operation onto the substrates on the tray is repeated. In this manner, 1,000 pieces of biochips on which 10,000 samples containing different DNA fragments are spotted can be prepared without producing satellites and the like. DNA microarrays with microspots having a high and constant quality can be obtained.

In still another modification of the present embodiment, although drawings are omitted, one may compose to use a plurality of robots being composed of a first moving table and a second moving table; wherein a tray with a substrate fixed thereon is mounted on a first moving table of one robot among a plurality of robots, the sample having been introduced into a cavity is discharged onto the predetermined points on a substrate as liquid drops from one discharge head mounted on a second moving table forming said one robot, while adjusting the relative positions of the substrate and the sample discharge port, thereby spots of the sample having been provided to said one discharge head is formed on the substrate, then the tray is removed, and the removed tray is mounted on a first moving table of another robot among a plurality of robots, the sample having been introduced into a cavity is discharged onto the predetermined points on the substrate as liquid drops from the other discharge head mounted on the other second moving table forming said other robot, thereby spots of the sample having been provided to said other discharge head is formed on the substrate, and repeat this procedure in a number of times equal to the number of the robots.

One may reduce a period of time for spotting all the spots, with employment of this composition, since spots are formed on the substrate while the tray moves between them, by using a plurality of robots being composed of a second moving table with a discharge head mounted thereon, in which a sample has previously been introduced, and a tray with a substrate fixed thereon. This manufacturing method is particularly suitable for the manufacture of biochips which requires processing biological samples within a limited period of time. In the case of biochips in which a great many types of spots are formed on one substrate, since it is physically impossible to form these spots using one discharge head, the spots must be formed using several discharge heads. This embodiment is effective in such a case. The above configuration using robots can be materialized by independently providing a discharge head 3, a tray 4, a first moving table 5, and a second moving table 6 as shown in FIG. 1.

In this embodiment, one may employ such a composition that spots are formed on another substrate fixed to another tray with the above-mentioned first robot, during a period when spots are being formed on the substrate, on which spots have been formed by using the first robot, by using another robot after forming spots on said substrate using the first robot.

The production speed and the productivity for a large number of biochips may be improved, by employing said composition. More specifically, because it is possible to perform spotting on a number of substrates using a plurality of trays by the application of a first robot until the entire amount of the sample introduced into one discharge head has been consumed, while performing an additional spotting operation onto the substrate on which the spotting has been completed using the first robot by the application of a second robot, precious samples can be utilized effectively and mass-production of biochips is possible.

In addition, the unit of this embodiment can be configured so that the position of the discharge head 3 in the absolute coordinates of the second moving table 6 is measured each time the discharge head 3 is mounted on the second moving table 6 and the position of the tray 4 in the absolute coordinates of the first moving table 5 is measured each time the tray 4 is mounted on the first moving table 5, as shown in FIG. 8. The relative positions of the discharge head 3 and the tray 4 is calculated from the measured results so that the spots may be formed by discharging the sample onto predetermined points on the substrates 2 fixed on the tray 4.

One may decrease deviation of the mounting position of the discharge head 3 and deviation of the mounting position of the tray 4, whereby positional accuracy of spots on the substrate may be improved, by thus composing as mentioned.

Specifically, the discharge head 3 is formed with a head reference mark 23 of a light-emitting device, as shown in FIG. 3(*a*). At every time when another discharge head (not shown) containing a sample of different type DNA fragments is installed, as shown in FIG. 8, the position of the discharge head 3 is aligned for discharge by adjusted the position of the discharge head 3 while observing the relative positions using a second table fixing reference 11 such as a CCD camera provided in a specified location under the discharge head 3 to prevent deviation of spotting positions due to misalignment of the discharge head 3 when the discharge head is replaced. As compared with head adjustment by observation of reflection light, direct observation of lights from a light-emitting device such as a CCD camera in this manner ensures observation unaffected by the surface conditions of the reflection body and excludes influence of disturbing external lights. Positioning accuracy can be improved in this manner. One may achieve to keep the deviation in the positions of ultimately produced spots within 50 μm of the designed value. Light emitting devices such as a photodiode can be used for forming such a reference mark. It is possible, however, to employ a method of observation comprising providing a hole and introducing lights through a separate fiber or prism.

If mechanical precision of the mounting section between the discharge head 3 and the second moving table 6 and between the tray 4 and the first moving table 5 is sufficiently improved to guarantee their constant mounting at the same positions, this type of configuration is unnecessary. This is, however, practically impossible in the manufacture of biochips which requires aligning of several tens to several tens of thousands of spots in a small area of several mm$^2$ to several cm$^2$ in an orderly manner without having any overlapping spots. For instance, when 1,005 pieces of biochips having one sheet of substrate 2 with 6,048 spots formed thereon is manufactured using a biochip-manufacturing apparatus 1 as shown in FIG. 1, wherein one discharge head 3 has 96 sample discharge ports and one tray 4 can secure 15 sheets of substrates 2 thereon, the installation-removal operation of the discharge head 3 on the second moving table 6 must be carried out 63 times (6,048/96) and the installation-removal operation of the tray 4 on the first moving table 5 must be carried out 4,221 times {(1,005/15)×63}. It is difficult to satisfy these conditions even if the mechanical accuracy of the mounting section for the discharge head 3 and the tray 4 is improved. Only the above-described measurement of positions and relative positions can provide biochips with spots aligned at high accuracy.

In performing the above-mentioned measurement of positions and relative positions, the positional deviations of the discharge head 3 and the tray 4 can be decreased even more by repeating the position measurement of the discharge head 3 with respect to the absolute coordinates of the second moving table 6 and the position measurement of the tray 4 with respect to the absolute coordinates of the first moving table 5 for an optional number of times, thereby correcting relative positions of the discharge head 3 and the tray 4. The positional accuracy can be further improved in this manner. For example, if spotting onto one tray 4 is carried out by correcting the positional deviation of the discharge head 3 each time the tray 4 is mounted on the first moving table, any minor positioning deviations of the discharge head 3 occurring as a result of a move of the discharge head 3 can be corrected each time the tray 4 is replaced.

Furthermore, in the above-mentioned measurement of the positions and relative positions, it is desirable to provide a head reference mark 23 in at least two predetermined locations of the discharge head 3 (see FIG. 3(a)) and a second table fixing reference 11 such as a CCD camera at two or more locations of an immovable part of the second moving table, measure the relative positions of the head reference mark 23 and second table fixing reference 11 at two or more locations, and apply the measured results to the correction of the mounting position deviation of the discharge head 3 by decomposing the direction and amount of the deviation in the longitudinal, lateral, and rotational directions.

The positional precision improves by measuring the positions at two and more points in this manner. Through the decomposition and correction of the direction and amount of deviation of the mounting position of the discharge head 3 in the longitudinal (Y), lateral (X), and rotational (θ) directions, calculation and correction become easy by offsetting in each of the directions to which the second moving table 6 moves.

In a more preferable manner of correction, the table reference mark 12 is provided at least at two points in the movable part of the first moving table 5 and the first table fixing reference 13 such as a CCD camera is provided at least at two points in the immovable part of the first moving table 5, to measure the relative positions of the table reference mark 12 and first table fixing reference 13 at least at two points; the tray reference mark 22 (see FIG. 4) is provided by forming a hole in at least two positions of the tray 4 to measure the relative positions of the tray reference mark 22 and the first table fixing reference 13 at two or more locations; and based on the measured results obtained, the direction and amount of deviation of the mounting position of the tray 4 are corrected by decomposing the deviation in the longitudinal and lateral directions.

In this manner, the deviation of the mounting position of the tray 4 with respect to the movable part of the first moving table 5 can be corrected by comparing the table reference mark 12 provided in the movable part of the first moving table 5 to the first table fixing reference 13 provided in the immovable part of the first moving table 5, and comparing the tray reference mark 22 (see FIG. 4) provided by forming a hole at a predetermined point of the tray 4 to the first table fixing reference 13. Therefore, the necessity of proving a first table fixing reference 13 such as a CCD camera in the movable part of the first moving table 5, of which the reference itself easily deviates, can be avoided. In addition, even in the case where the first table fixing reference 13 itself, which is provided in the immovable part of the first moving table 5, deviates, the correction, not affected by the corrections of the positional deviation of the tray 4 with respect to the movable part of the first moving table 5, is possible. More accurate correction is possible in this manner. One may improve the positional precision, by comparing these positions at two and more points. In addition, through the decomposition and correction of the direction and amount of deviation in the longitudinal direction (Y) and lateral direction (X), correction can be carried out easily by offsetting in each of the directions to which the first moving table 5 moves.

Figure 9:
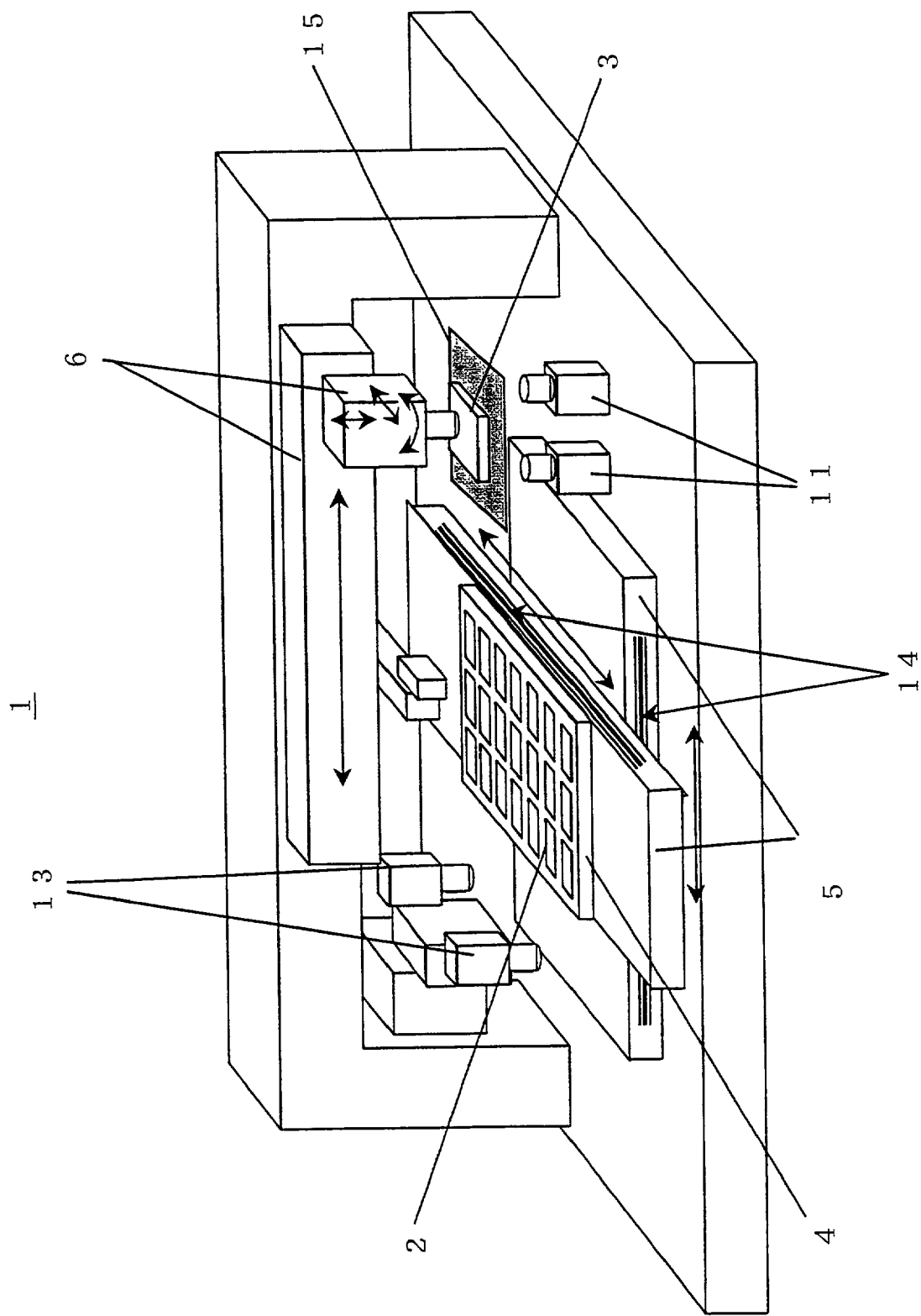
FIG. 9 is a perspective view showing a configuration of a biochip-manufacturing apparatus used in still another embodiment of the biochip manufacturing method of the present invention.

In addition, in this embodiment, as shown in FIG. 9, at least one of the first moving table 5 or the second moving table 6 can be moved while correcting using an outside reference 14 provided in the immovable part of at least one of the first moving table 5 or the second moving table 6.

Since the absolute precision for the movement of the first moving table 5 and the second moving table 6 can be improved since the decision of the positions at which spots may be done formed with respect to the outside reference 14, by composing so. This is particularly effective in the manufacture of biochips which requires aligning several tens to several tens of thousands of spots in a small area of several $mm^2$ to several $cm^2$ in an orderly manner without having any overlapping spots.

The absolute precision for the movement of the first moving table 5 or the second moving table 6 can be also increased by combining the above-mentioned correction of positional deviation for the discharge head 3 and the tray 4. In this manner, the positional precision for the spot arrangement can be further improved, resulting in further improvement of the biochip quality.

The above-mentioned correction of the positional deviation for the discharge head 3 and tray 4 is performed based on the comparison between the head reference mark 23 (see FIG. 3(a)) and the second table fixing reference 11 (see FIG. 8), the comparison between the table reference mark 12 (see FIG. 8) and the first table fixing reference 13 (see FIG. 8), and the comparison between the tray reference mark 22 (see FIG. 4) and the first table fixing reference 13 (see FIG. 8), and by calculating the positional relationship of these elements. In the case of the biochip manufacturing method according to this embodiment, wherein a number of discharge heads 3 and trays 4 are provided to produce high density spotting by discharging the sample while the discharge heads 3 and the trays 4 are brought close to each other, direct comparison of the head reference mark 23 (see FIG. 3(a)), the table reference mark 12 (see FIG. 8), and the tray reference mark 22 (see FIG. 4) is impossible because of too many physical limitations to the means of observing the discharge head 3 and the tray 4 at the same time. For this reason, the method of independently measuring the discharge head 3 and the tray 4 using the first table fixing reference 13 and the second table fixing reference 11, such as a CCD camera, provided in the immovable part, and then comparing and calculating their positional relationship is more suitable. In such a case, the use of the outside reference 14, shown in FIG. 9, is effective to correct the movement of the first moving table 5 and the second moving table 6.

The outside reference 14 is preferably a reference gauge composed of a material with a low thermal expansion coefficient. The spot-positioning accuracy is increased since the effect of temperature variations, change of properties with time, and change in the XY orbit resistance may be kept in a lower level by composing so. In particular, when a large number of biochips is manufactured, the first moving table 5 and the second moving table 6 must be continuously operated for such a long time that movable parts of these tables are heated, causing their parts and components to swell. As a result, the positional accuracy of the trays 4 and discharge heads 3 mounted on these tables is impaired. In such a case, swelling of the parts and components can be decreased by using a material with a low thermal expansion coefficient, whereby the production yield of biochips, which require aligning several hundreds of thousand to several tens of thousand spots in a small area of several $mm^2$ to several $cm^2$ in an orderly manner without having any overlapping spots, can be increased.

In addition, it is preferable in this embodiment that the first moving table 5 and the second moving table 6 be moved while adjusting the relative positions of the substrate 2 and the sample discharge port so that the discharge head 3 and the tray 4 are brought to predetermined positions, and then the sample be discharged from the sample discharge port to form spots in the state in which the discharge head 3 and the tray 4 stop.

By composing so, environmental conditions (wind, vibration, etc.) around the sample discharge port for each spot become invariable and uniform, the shapes of discharged liquid droplets are stabilized, and accordingly the form of the spots on the substrate 2 is stabilized. Specifically, regarding the relationship between the moment of discharge and the moving time of the discharge head 3 and the tray 4, it is preferable that the sample be discharged at the moment when these are brought to desired relative positions while the tray 4 is moving in the XY direction or the discharge port 3 is moving in the Z direction to decrease the time required for spotting. However, to exclude the influence of the above-described external disturbances such as wind and vibration, it is possible to discharge the sample after the discharge head 3 and the tray 4 a have stopped in the desired relative positions.

In the embodiment shown in FIG. 3(*a*) and FIG. 4, in which a discharge head 3 equipped with a plurality of discharge modules 7 and a tray 4 with a plurality of substrates 2 fixed thereon is used, the tray 4 is moved to have a predetermined positional relationship with the discharge head 3, while simultaneously adjusting the relative positions of the sample discharge ports for all discharge units 8 in one discharge module 7 and one substrate 2*a* among a plurality of substrates 2 fixed on the tray 4; the sample stored in one discharge module 7*a* is discharged onto one substrate 2*a* from the sample discharge ports for all discharge units 8*a* in said one discharge module 7*a*, thereby forming spots corresponding to the sample discharge ports for all discharge units 8*a* in said one discharge module 7*a*; next, the tray 4 is moved to establish a predetermined positional relationship between one substrate 2*a* and the sample discharge ports of all discharge units 8*b* in another discharge module 7*b*, while simultaneously adjusting the relative positional relationship between the substrate 2*a* and the sample discharge ports of all discharge units 8*b* in said other discharge module 7*b*, the sample stored in said other discharge module 7*b* is discharged onto the one substrate 2*a* from the sample discharge ports for all discharge units 8*b* in said other discharge module 7*b*, thereby forming spots corresponding to the discharge ports for all discharge units 8*b* in that another discharge module 7*b*; this process is repeated for a number of times equal to the number of discharge modules 7 arranged in the discharge head 3, thereby forming spots on said one substrate 2*a* corresponding to sample discharge ports for all discharge units 7 present in the discharge head 3; then the tray 4 is moved to secure another substrate 2*b* on the tray 4 and spots are formed corresponding to sample discharge ports for all discharge units 8 present in the discharge head 3; and the process is repeated for a number of times equal to the number of substrates 2 fixed on the tray 4; wherein the discharge operation intervals of the discharge units 8 in a number of discharge modules 7 are preferably almost equivalent.

In this manner, the sample can be discharged simultaneously from all discharge units 8 in the discharge module 7 by implementing the operations of movement, position adjustment, and spotting on one sheet of substrate 2 for each discharge module 7. Therefore, spotting speed is increased. In addition, if the positioning accuracy of each discharge unit 8 in the discharge module 7 is previously increased by a mechanical means, it is possible to simultaneously align a plurality of discharge units 8 on a discharge module 7. The spotting speed and the positioning accuracy in the entire process can be improved in this manner.

Since one discharge head 3 is composed of a plurality of discharge modules 7, the number of discharge units 8 per one discharge head 3 can be increased. In addition, the method can easily handle an increased number of samples. Using this configuration, it is possible not only to increase the number of discharge units 8 in one discharge head 3 by increasing the number of discharge modules 7 without increasing the density of the discharge units 8 themselves, but also to increase the types of samples which are processed in one discharge head 3. The production efficiency is improved in this manner.

Furthermore, it is possible to maintain constant drying conditions for the samples waiting for discharge near the sample discharge ports, as well as the moving conditions of the sample before discharge, by maintaining the interval of the discharge operation of discharge units 8 in different discharge modules 7 constant. This ensures homogeneous liquid properties of the sample at the time of discharge, stabilizes the discharge direction, and produces spots with a uniform shape on the substrate 2.

In this instance, when the sample stored in one discharge module 7*a* is discharged onto one substrate 2*a* from the sample discharge ports for all discharge units 8*a* in said one discharge module 7*a*, thereby forming spots, then the tray 4 is moved to establish a predetermined positional relationship between the one substrate 2*a* and the sample discharge ports of all discharge units 8*b* in other discharge modules 7*b*, while simultaneously adjusting the relative positional relationship between the substrate 2*a* and the sample discharge ports of all discharge units 8*b* in those other discharge modules 7*b*; and after forming spots on said one substrate 2*a* using the sample from the sample discharge ports for all discharge units 8 in the discharge head 3, when the tray 4 is moved to establish a predetermined positional relationship between the other substrate 2*b* and all sample discharge ports of the other discharge units in other discharge modules for forming spots on that other substrate 2*b*, while adjusting the relative positional relationship between the substrate 2*b* and the sample discharge ports of all discharge units 8*a* in those other discharge modules 7*a*, the discharge head 3 is preferably maintained stopped.

In this manner, by moving only the tray 4 while keeping the discharge head 3 stationary, unnecessary vibration to the discharge head 3 and airflow disturbance can be avoided. Discharge of liquid drops can be stabilized producing biochips with a stable spot configuration.

Figure 17:
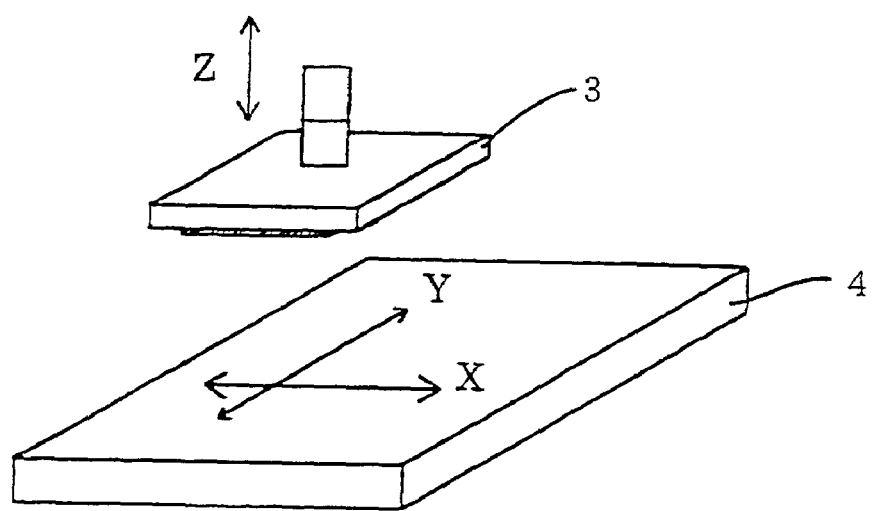
FIG. 17 is a perspective view schematically showing the manner for changing relative locations of a tray and a discharge head.

In this instance, the relative positions of the tray 4 and the discharge head 3 can be preferably changed by securing the discharge head 3 in the XY directions on the plane and moving the tray 4 on which the substrates are fixed, as shown in FIG. 17. In the formation of micro spots by discharging a sample from the biochip-manufacturing apparatus of this embodiment, the movement of the discharge head results in subjecting the fixed discharge unit 8 (see FIG. 3(*a*)) to external disturbances such as vibration, airflow, and the like. Such external disturbances may change the state of the liquid surface at the discharge port of the discharge unit 8 (see FIG. 3(*a*)), which may give rise to fluctuation in the amount and direction of discharge of liquid drops. In addition, the fluid sample may become dry and cause discharge malfunction. Discharge of samples while the discharge head 3 is moving brings about many disadvantages in accurately controlling spotting positions. This is because the discharged fluid droplets are provided with a velocity in the XY direction corresponding to the moving speed of the discharge head 3 at the time of discharge, which may affect the point on the glass slide which the spot reaches. Therefore, a preferable method is to discharge the sample and produce spots when the discharge head 3 and tray 4 are brought to desired relative positions in the XY direction by moving the tray 4.

Fixing the location of the discharge head 3 in the XY direction while changing the position relative to the tray 4 is desirable in securing consistent emission of discharge signals because cables delivering signals to the discharge head 3 are not affected by vibration and the like if the discharge head 3 is fixed in a fixed position, thereby suppressing changes in the cable characteristics such as impedance due to twisting. Consequently, consistent discharge of drops, specifically, quality improvement of the DNA microarray, can be achieved. It is possible to move the discharge head 3 in the vertical direction (Z direction) with respect to the tray 4 and reduce the distance between the sample discharge port of the discharge unit 8 (see FIG. 3(*a*)) and the substrate 2 (see FIG. 1), i.e. the distance in the Z direction vertical to substrate 2, only at the moment of discharge.

In addition, it is preferable to vertically remove the discharge head 3 from the tray 4 before moving the tray 4, and after moving the tray 4, to move the discharge head 3 to vertically approach the tray 4.

The discharged liquid drops are prevented from being damaged, by composing so, even if foreign substance is attached to the substrate 2 (see FIG. 1) and the discharge head 3. In addition, the effect of the curved discharge direction when liquid droplets are discharged from the discharge unit on the spot-forming points can be reduced by shortening the distance between the substrate 2 (see FIG. 1) and the discharge head 3. The degree of spot-forming point deviation can be reduced in this manner.

In the present embodiment, the sample is preferably discharged from the discharge units at regular intervals merely for the purpose of dummy discharge during the time other than the period in which a series of operations for forming spots on specified points on substrates by discharging samples from the sample discharge ports takes place.

This can prevent drying of sample flow routes during a period of time when the samples are not discharged to substrates and ensure stable sample discharge even in the case where the biochip-manufacturing apparatus is operated for a long period of time.

In this instance, the intervals of the dummy discharge is preferably almost the same as the intervals of the sample discharge, beginning from before the time when a series of operations is started for forming spots on specified points on substrates by discharging samples from the sample discharge ports. By composing so, drying conditions of the samples waiting for discharge near the sample discharge ports as well as the moving conditions of the sample before discharge become constant, accordingly, sample properties at the time of discharge become equal. This stabilizes the discharge direction, stabilizes the state of discharged liquid droplets, and produces spots with a uniform shape on the substrate 2.

Figure 14:
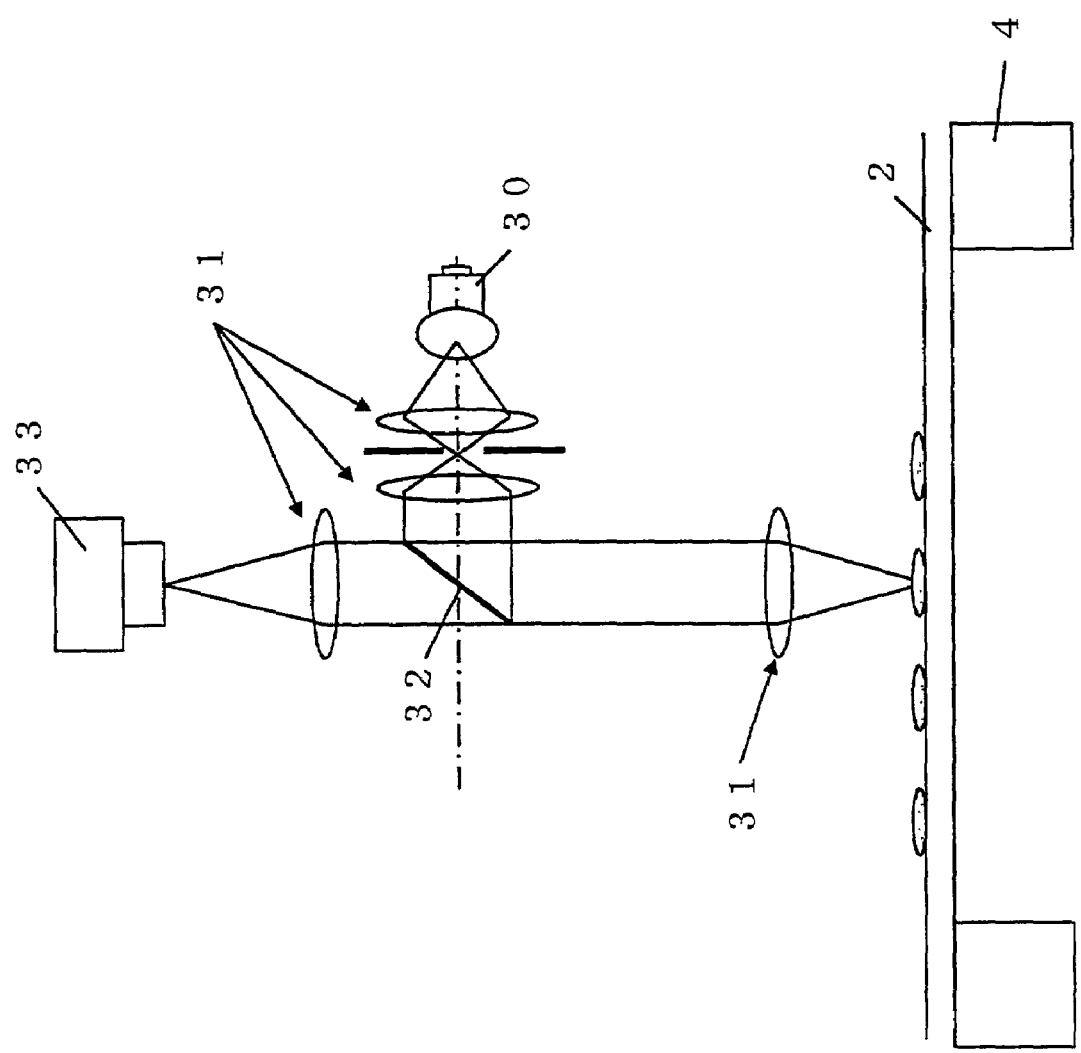
FIG. 14 is a drawing for illustrating a spot shape inspection device used in the biochip manufacturing method of the present invention.

In a still further preferred embodiment, after forming spots on predetermined points of the substrate 2 by discharging a sample from the sample discharge ports, the substrate 2 is irradiated with a coaxial light 30, converged using a lens 31 as shown in FIG. 14. A spot configuration is determined by the image produced by reflection of light on the surface of the substrate 2 on which spots have been formed, thereby accumulating propriety information for the spots. In FIG. 14, the substrate 2 fixed on the tray 4 is irradiated with a coaxial light 30 emitted from the side and reflected by a half mirror 32 and a photograph is taken from the top by a CCD camera. The configuration, however, is not limited to that shown in FIG. 14. Any system capable of taking images on the substrate 2 on which spots have been formed may be applied.

Such a system makes it possible to view the shape of spots made from a transparent liquid sample such as a DNA solution as a shadow produced by the difference of light reflection angles at the edges of the spots. Since the spot quality can be easily determined using this system, a substrate 2 with a defective spot can be easily excluded, whereby the biochip quality can be improved.

Figure 15:
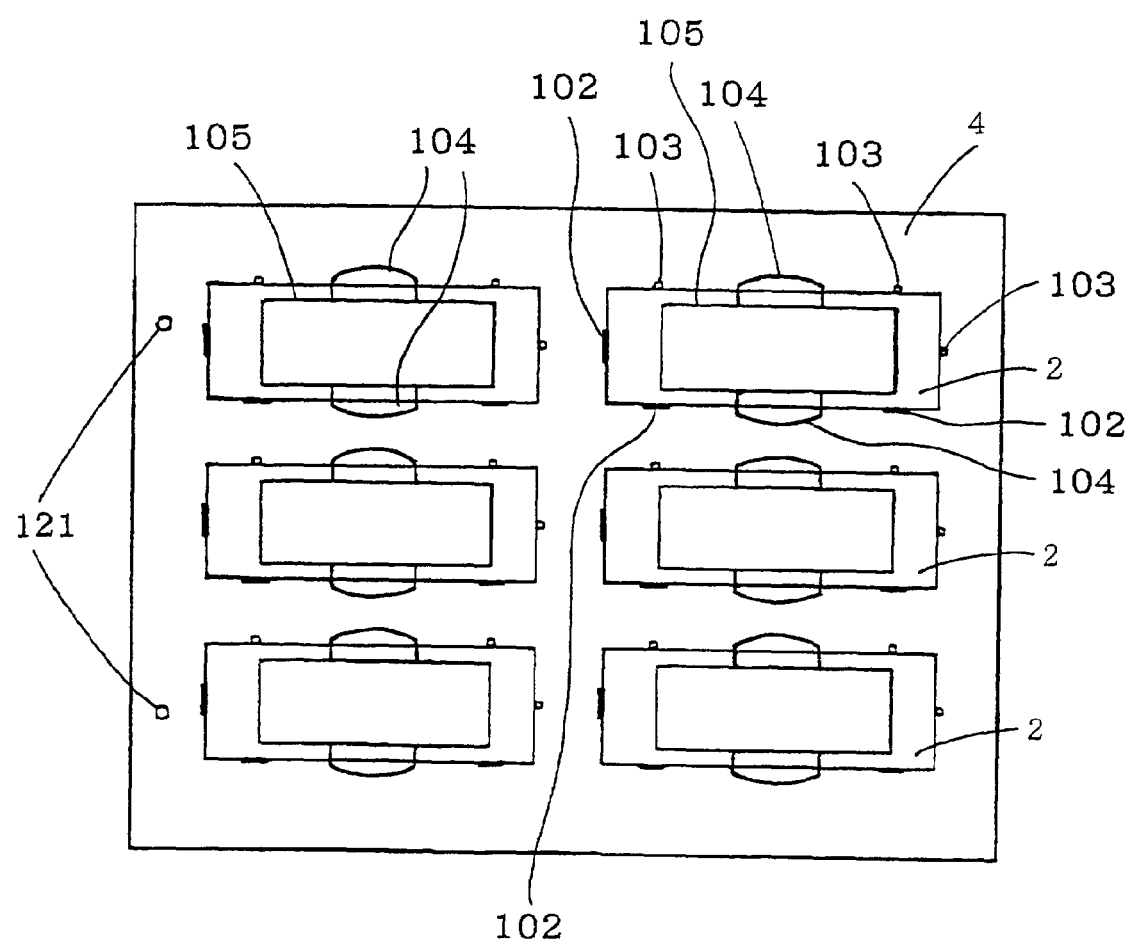
FIG. 15 is a plan view schematically showing a tray used in a further embodiment of the biochip manufacturing method of the present invention.

Although the substrate 2 may be fixed to a tray 4 by means of adhesion using adhesive tape, silicone rubber, etc., or fixed by suction, for example by using vacuum suction, a more preferable method is a mechanical securing method using board springs 102 and pins 103 as shown in FIG. 15. This method ensures accurate securing by a simple means without causing adhesive residues to be attached to the substrate 2 and without enlarging the scale of facilities for the tray 4.

Figure 16:
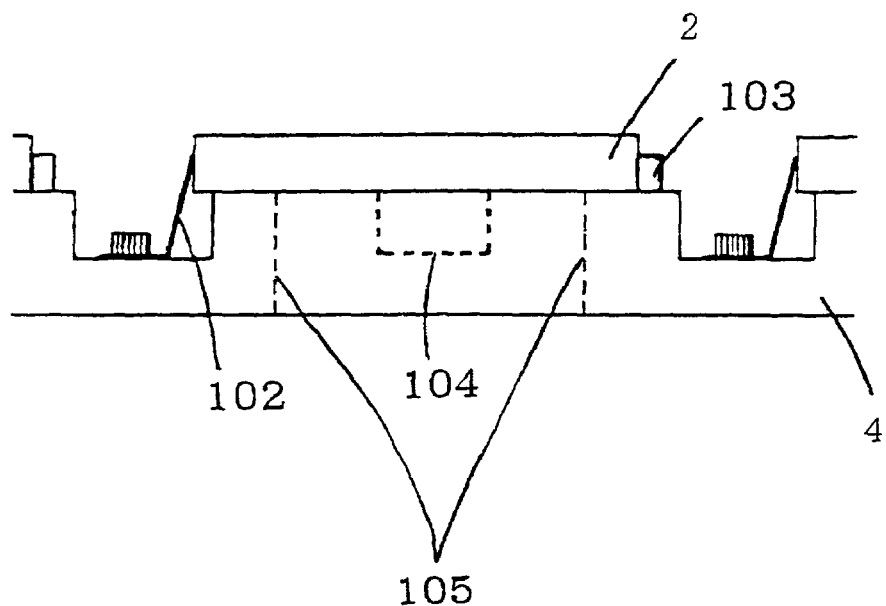
FIG. 16 is a cross-sectional view schematically showing the manner of mechanically securing a substrate to a tray using a board spring and a pin.

The positions, number, and the like of the pins 103 and board springs 102 to secure the substrate 2 are appropriately determined according to the slipping properties of the tray 4 and substrate 2, strength of the board springs 102, thickness of the substrate 2, and other factors. Securing the substrate 2 using three pins 103 as shown in FIGS. 15 and 16 is desirable in view of precision.

In addition, the tray 4 may be previously provided with an opening 104 for ease of attachment and removal of the substrates 2 in locations wherein the substrates 2 are placed. The area 105 on the surface of the tray corresponding to the part of the substrate 2 on which spots are formed is made hollow and linked to the bottom surface of the tray 4.

This structure makes a light tray 4 and increases the biochip production efficiency. In addition, the structure is advantageous for maintaining and improving quality of the biochips because such a structure enables the manner by which spots are formed to be observed inline from the bottom surface of the tray 4 through the hollow space. When measuring the shape of spots based on images produced by reflection of light from the substrate 2 on which spots have been formed as mentioned above, the configuration having a hollow space has the merit of absence of any light reflection on the tray surface. The measurement is easier. The hollow space may be cut concave and, to exhibit the above advantage, preferably has a bottom surface processed so as not to reflect light.

As described above, according to the method of manufacturing biochips of the present embodiment, the operation of densely aligning and fixing droplets with a minute volume on a predetermined substrate (micro spot-forming operation) can be performed with increased precision, thereby shortening the time required for the micro spot-forming operation. An increased spot positioning accuracy and spot density can reduce the area for the spots. Therefore, the effect of fluctuations of a coating used for immobilizing DNA samples on a substrate on the spotting operation can be reduced, leading to improved biochip quality. In addition, the amount of expensive reagent, such as a hybrid fluid, used for inspecting DNA samples contained in the spotting liquid (the sample) can be reduced.

EXAMPLE 1

Figure 6:
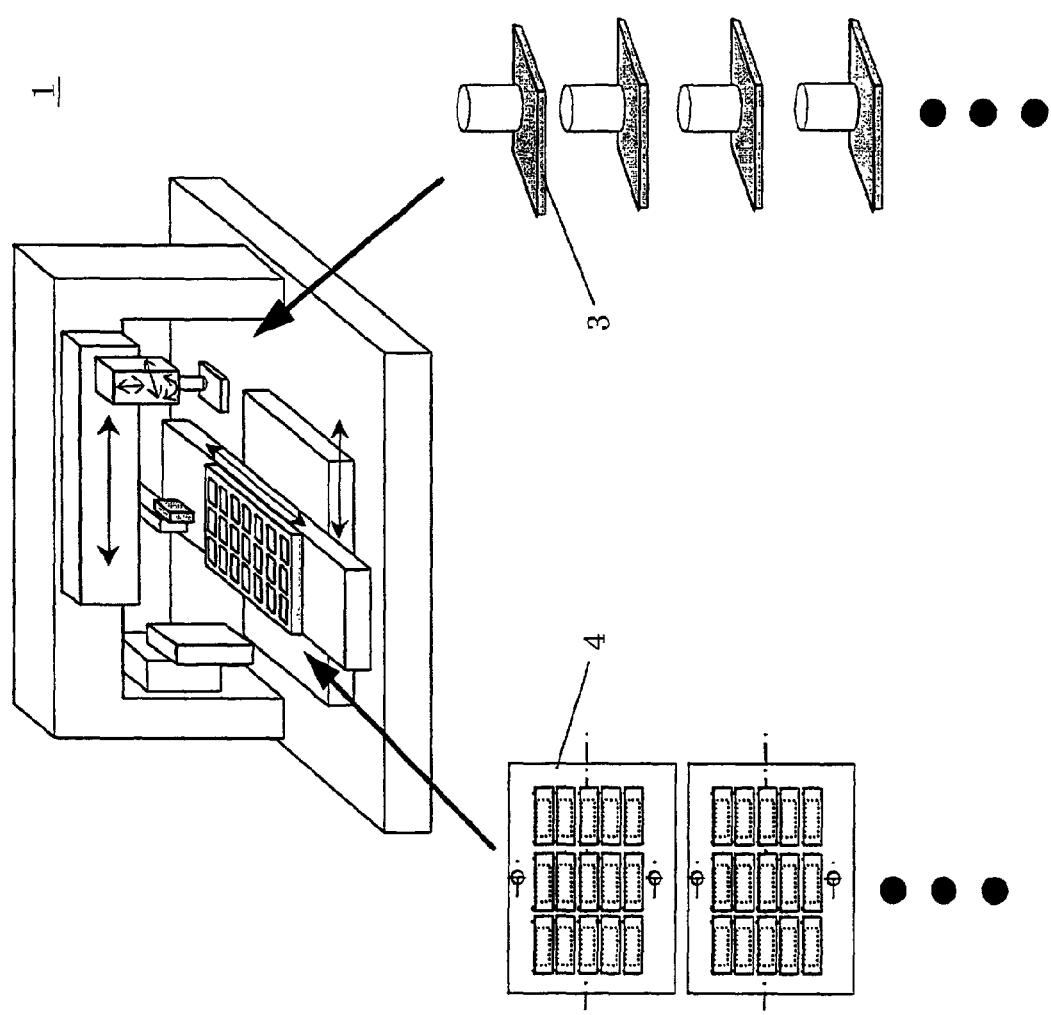
FIG. 6 is a drawing for illustrating an outline of installing and replacing the discharge head and tray of a biochip-manufacturing apparatus used in one embodiment of the biochip manufacturing method of the present invention.

Biochips were prepared using a biochip-manufacturing apparatus 1 shown in FIG. 1 on which a discharge head 3 of FIG. 3(a) and a tray 4 of FIG. 4 are mounted. The tray 4 was previously provided with an opening 104 for ease of attachment and removal of the substrates 2 in locations wherein the substrates 2 are placed, and has a hollow space on the surface 105 of the tray in the area corresponding to the substrate 2 on which spots are formed, wherein the hollow space goes through the bottom of the tray 4, as shown in FIGS. 15 and 16. As shown in FIG. 6, the tray 4 and discharge head 3 are detachably mounted on the biochip-manufacturing apparatus 1.

Figure 7A:
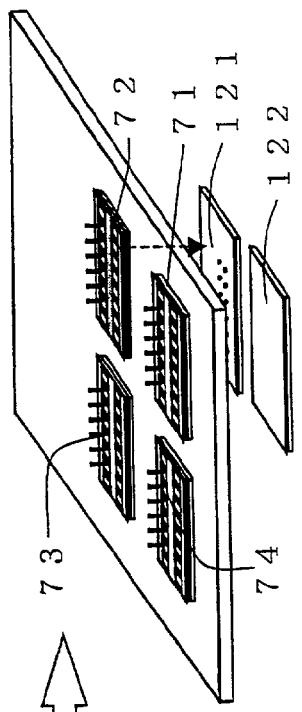
FIGS. 7(a) to 7(d) are drawings for illustrating a step of adjusting the relative positions of the substrate and discharge head and forming spots on the substrate for each module in one embodiment of the biochip manufacturing method of the present invention.
Figure 7B:
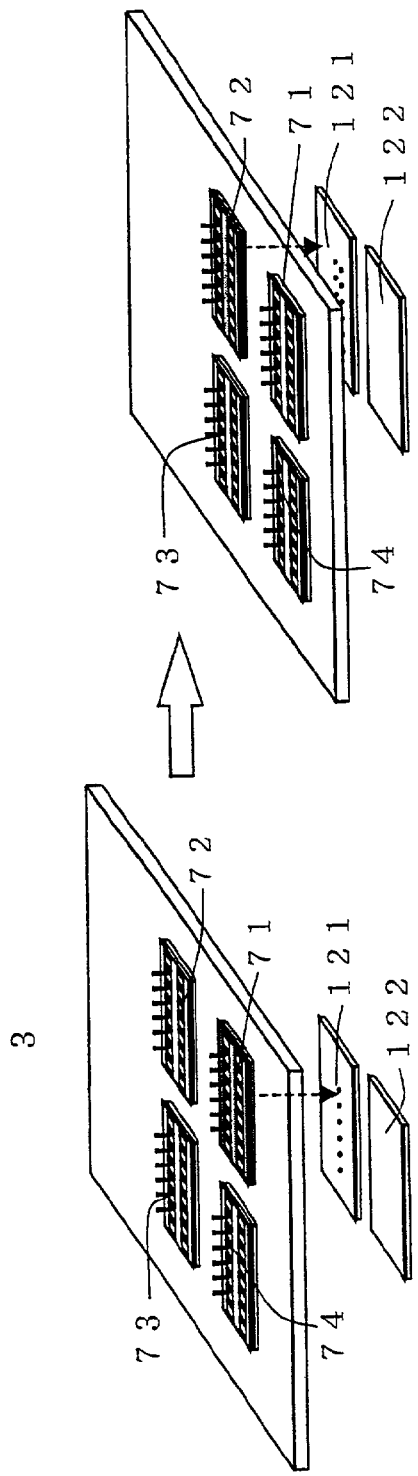
Figure 7C:
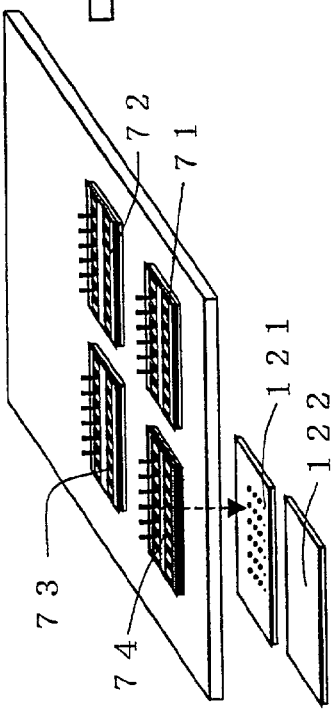
Figure 7D:
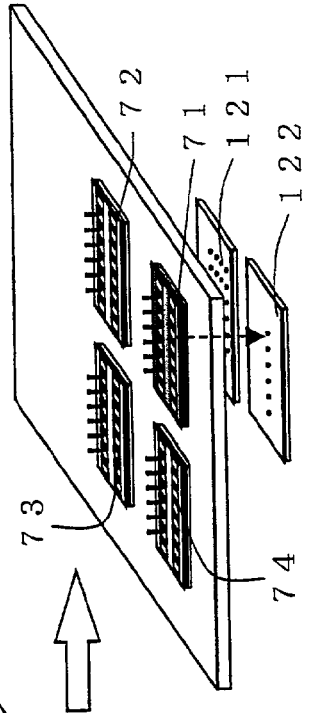

The samples were discharged in the following manner. Specifically, the samples were discharged from the discharge module 71 of the discharge head 3 after moving the substrate 121 as shown in FIG. 7(a). Then, the substrate 121 was moved as shown in FIG. 7(b) and the samples were discharged from the discharge module 72 of the discharge head 3 to locations different from the locations in which the samples had been discharged by the discharge module 71. In the same manner, the substrate 121 was moved and the samples were discharged from the discharge module 73 of the discharge head 3 to locations different from the locations in which the samples had been discharged by the discharge modules 71 and 72. Next, the substrate 121 was moved as shown in FIG. 7(c), and the samples were discharged from the discharge module 74 of the discharge head 3 to locations different from the locations in which the samples had been discharged by the discharge modules 71, 72, and 73. Spots were formed by repeating the operation of discharging samples from the discharge module 71 onto the substrate 122, as shown in FIG. 7(d).

In this example, 4 discharge heads 3, each having 4 discharge modules 7, each of which is provided with 6 discharge units, as shown in FIG. 3(a), were used. In addition, 20 trays 4, each capable of securing 15 sheets of substrates 2 thereon, as shown in FIG. 4, were used. A sample was charged to each discharge head 3, which was installed on the second moving table 6, and the tray 4 was installed on the first moving table 5, as shown in FIG. 1. Samples were discharged to each substrate 2 on each tray 4, and the discharge head was washed. This procedure was repeated five times. A biochip with 480 kinds of samples spotted on one sheet of substrate was prepared in this manner. 300 pieces of such a biochip were produced in 5 hours without unstable sample discharge.

EXAMPLE 2

Biochips were prepared using a biochip-manufacturing apparatus 1 shown in FIG. 8. Four discharge heads 3, each equipped with 4 discharge modules 7 in one discharge head 3, with head reference marks 23 provided thereon, wherein each discharge module 7 is provided with 6 discharge units, as shown in FIG. 3(a), and 20 trays 4, with tray reference marks 22 provided thereon, wherein each tray 4 can secure 15 sheets of substrate 2 thereon, as shown in FIG. 4, were used. Samples were charged to the discharge units of each discharge head 3, which was installed on the second moving table 6, and the tray 4 was installed on the first moving table 5. The amount of correction was calculated by comparing the relative positions of each reference mark and each reference, and the table movement taking into account the amount of correction was repeated. Sample discharge onto the substrates 2 on each of the trays 4 and the subsequent washing of discharge heads was repeated 25 times. A biochip with 2,400 different kinds of samples spotted on one sheet of substrate was prepared in this manner. Biochips were manufactured while measuring deviations of installation of each head and tray, each time these were installed, by comparing the head reference marks 23 (see FIG. 3(a)) to the tray reference marks 22 (see FIG. 4) and by comparing the first table fixing reference 13 and the second table fixing reference 11. 300 pieces of biochips with a spot positioning precision of ±20 μm were manufactured within 24 hours without unstable sample discharge.

EXAMPLE 3

Figure 10:
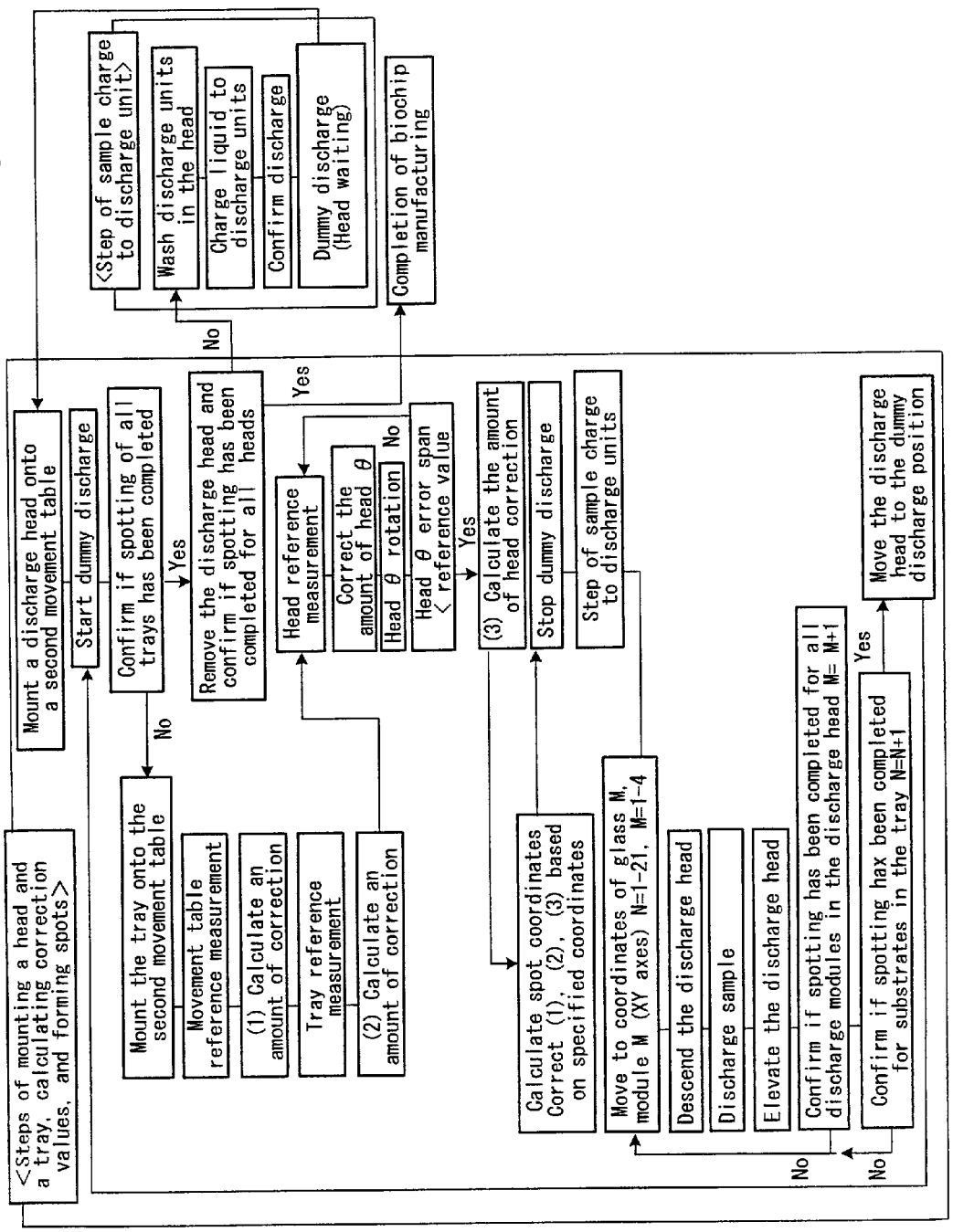
FIG. 10 is a flowchart showing the manufacturing process flow when one biochip-manufacturing apparatus is used in Example 3.
Figure 11:
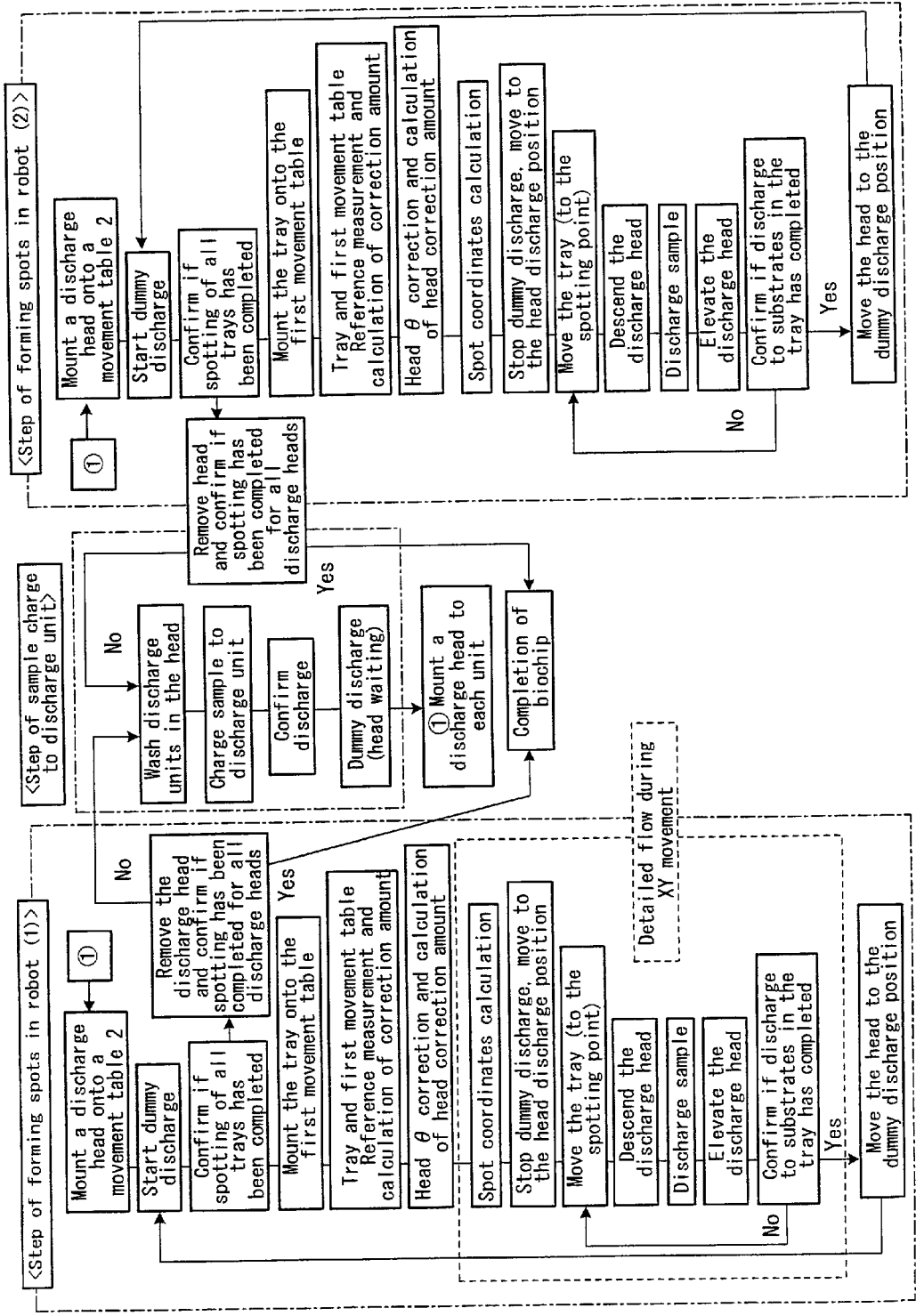
FIG. 11 is a flowchart showing the manufacturing process flow when two biochip-manufacturing apparatuses are used in Example 3.
Figure 12:
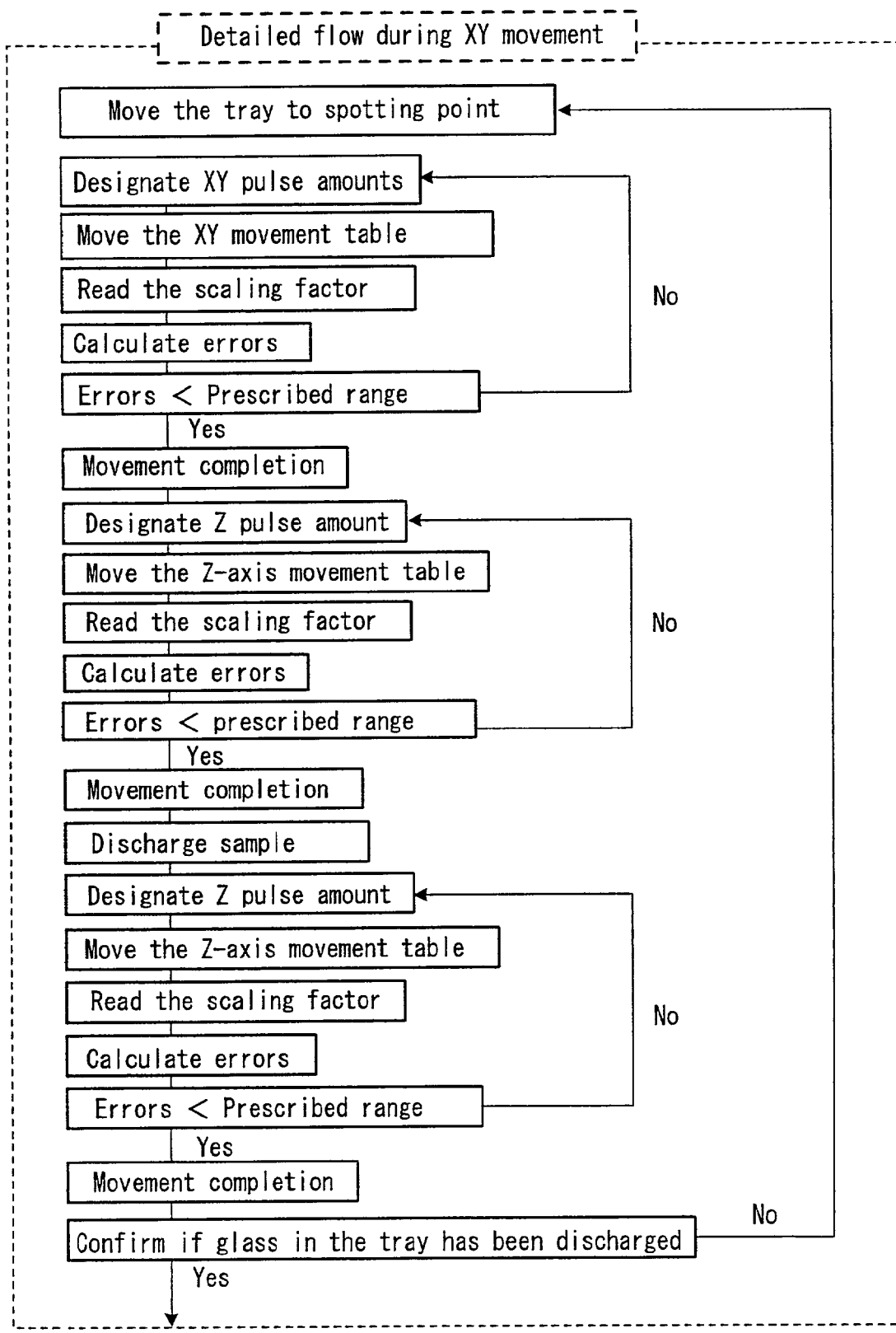
FIG. 12 is a part of the flowchart shown in FIGS. 10 and 11 showing details of an area for carrying out correction of a moving amount using an outside reference.
Figure 13:
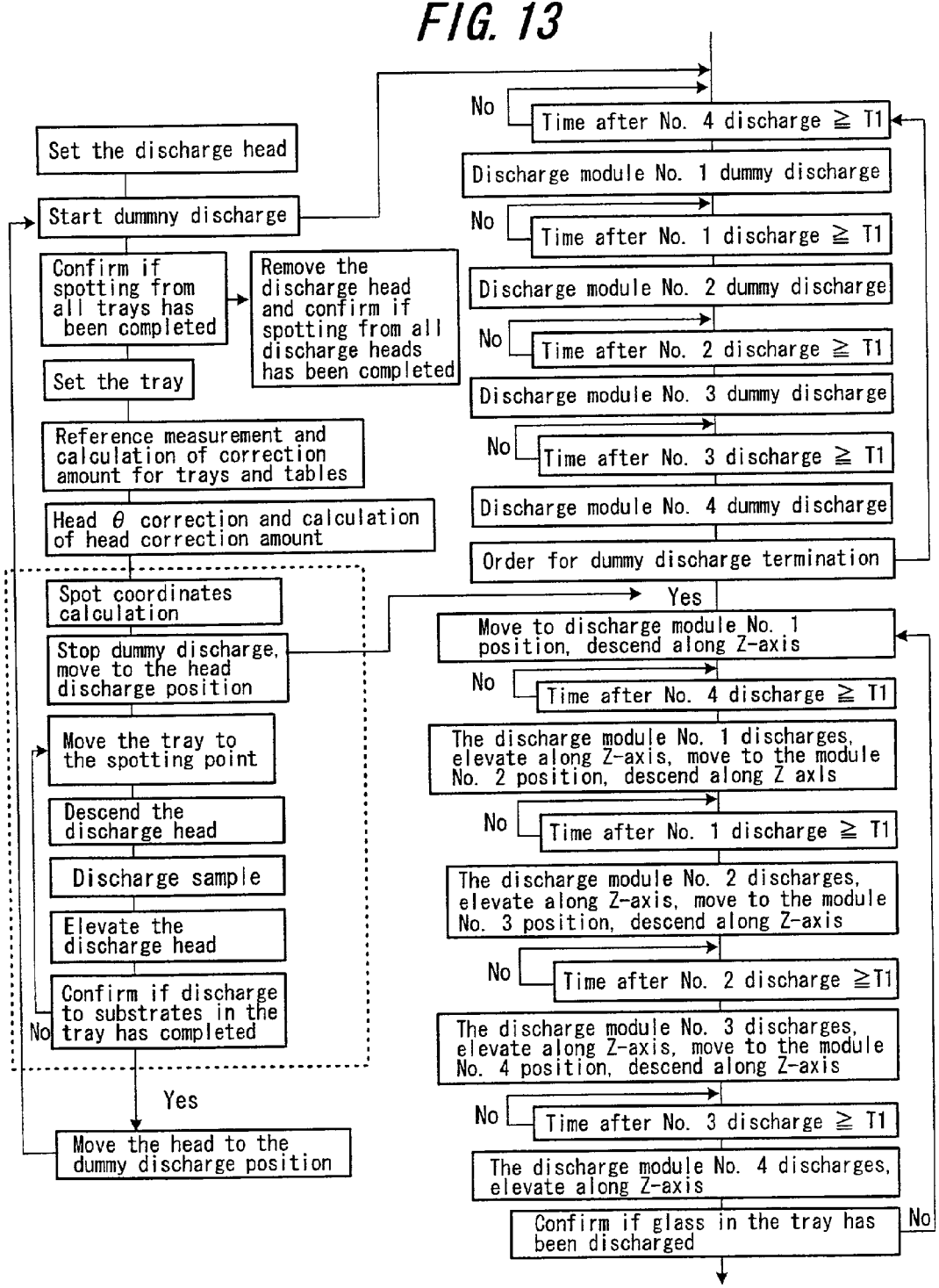
FIG. 13 is a part of the flowchart shown in FIGS. 10 and 11 showing details of discharge timing which is controlled for each discharge module.

Biochips were manufactured using the biochip-manufacturing apparatus 1 shown in FIG. 9, wherein the above-described process was employed. The manufacturing procedure when one biochip-manufacturing apparatus 1 was used is shown in the flowchart of FIG. 10, and that using two biochip-manufacturing apparatus 1 is shown in the flowchart 11. FIG. 12 is a part of the flowchart shown in FIGS. 10 and 11 showing details of an area for carrying out correction of a moving amount of the first moving table 5 during movement in the XYZ directions using an outside reference 14. FIG. 13 is a part of the flowchart shown in FIGS. 10 and 11 showing details of discharge timing which is controlled for each discharge module 7 (see FIG. 3(a)).

Four discharge heads, each containing 4 discharge modules, wherein each discharge module is provided with 48 discharge units, and 50 trays, each having 21 sheets of substrates fixed thereon, were used to prepare biochips, each formed from a sheet of substrate with 3,000 kinds of different samples spotted thereon. 1,000 pieces of such a biochip was manufactured in 11 hours using the process shown in the flowchart of FIG. 10. In the manufacture according to the flowchart of FIG. 11 using two tables, a first moving table and a second moving table, the same number of biochips was manufactured in 6 hours. A spot positioning precision of ±10 μm was achieved.

After charging the samples to the discharge units of discharge heads, dummy discharge was performed at regular intervals, excluding the period during which the samples were discharged onto substrates. The interval T for dummy discharge is specified by the dummy discharge parameter T1 shown in the discharge timing flow shown in FIG. 13. As shown in the flow, dummy discharge was also carried out for each module as in the case of sample spotting onto the substrates. A constant dummy discharge interval was maintained by employing the same parameters T1 to T4. Also for the spotting interval parameters T5–T8, the same T5–T8 parameters were used to ensure stable spotting quality.

By using the same parameters T1–T4 and the same parameters T5–T8, fluctuation of spotting quality can be minimized even immediately after shifting the discharge operation from dummy discharge to spotting discharge onto substrates. Stable spotting was achieved.

The means for correcting deviation of the mounting position was used for removing and installing the discharge head and tray in the same manner as in Example 2. The moving amount of the first moving table was corrected using the outside reference shown in FIG. 12. After completion of discharge by each discharge head, the resulting spot configuration was inspected using the instrument shown in FIG. 14. As a result, in the spotting operation of a sample containing a chemical agent specifically reacting with a transparent sample and providing information relating to the structure and functions of the specimen, the spot configuration was clearly observed and the data concerning the spot positions and shapes was acquired and accumulated.

As described above, the operation of densely aligning and fixing droplets with a minute volume on a predetermined substrate (micro spot-forming operation) can be performed by using the method of the present invention with increased precision, thereby shortening the time required for the micro spot-forming operation.

What is claimed is:

1. A method for manufacturing a biochip with spots of plural kinds of samples densely aligned on a substrate, wherein a sample containing a reagent specifically reactive with a specimen and providing information relating to the structure and functions of the specimen is introduced into a cavity via a sample charge port of a discharge unit having a sample charge port, a cavity, and a sample discharge port formed thereon, a substrate is provided at the position facing to the sample discharge port, the sample having been introduced into the cavity is discharged onto the substrate from the sample discharge port as droplets with a very small volume, thereby forming spots on the substrate, and the process is repeated for a plural kinds of the above-mentioned samples;

said biochip manufacturing method comprising the steps of:

providing a discharge head equipped with one or more discharge modules each of which being formed from one or more discharge units, providing means for rotating said discharge head by an angle of $\theta$ to correct for deviations in the rotational position of the discharge head;

introducing at least one of said plural kinds of samples into a cavity from a sample charge port of the discharge unit in the discharge head, so that one discharge unit is provided with only one kind of sample, providing a first moving table, on which one or more trays with one or more substrates fixed thereon are detachably mounted, said first moving table being movable along two axes within the plane of at least one substrate, transferring said first moving table to a sample discharge point of the discharge unit corresponding to a predetermined point on the substrate, and discharging the sample having been introduced into the cavity from the sample discharge port to a predetermined point on the substrate as liquid droplets, thereby spots of plural kinds of samples are densely aligned on the substrate.

2. The biochip manufacturing method according to claim 1, wherein the first moving table on which the tray being placed and a second moving table on which the discharge head being detachably mounted are provided, and the relative position of the substrate and the sample discharge port is adjusted.

3. The biochip manufacturing method according to claim 1, wherein each of said plural kinds of samples is individually introduced into the cavity by charging it from the charging port of the corresponding discharge unit, and one of the samples introduced into the cavity is discharged as liquid droplets onto a predetermined point on the substrate, thereby forming spots on the substrate, and this process is repeated for the plural kinds of samples.

4. The biochip manufacturing method according to claim 1, wherein at least one sample among said plural kinds of samples is introduced into the cavity by charging it from the charging port of the discharge unit of the discharge head so that only one kind of sample is provided to one discharge module, and said one sample introduced into the cavity is discharged as liquid droplets onto a predetermined point on the substrate, thereby forming spots on the substrate, and this process is repeated for the above plural number of samples.

5. The biochip manufacturing method according to claim 2, which comprises, provide two or more discharge heads, introducing at least one sample among said plural kinds of samples into the cavity by charging it from the sample charge port of each discharge unit of each discharge head, mounting one discharge head into which the sample has been introduced on the second moving table, discharging the sample having been introduced into the cavity onto the predetermined point on the substrate as liquid drops, with adjusting the relative position of the substrate and the sample discharge port of said one discharge head, thereby forming spots of the sample on one substrate, removing said one discharge head from the second moving table, mounting another discharge head into which a sample different from said sample has been introduced on the second moving table, discharging this different sample having been introduced into the cavity onto the predetermined point on the substrate as liquid drops, with adjusting the relative position of the substrate and the sample discharge port of said one discharge head, thereby forming spots of the sample on one substrate, and repeating the process a plural number of times equal to the number of discharge heads.

6. The biochip manufacturing method according to claim 2, which comprises, providing plural number of trays, mounting one tray among the plural number of trays on the first moving table, discharging the sample having been introduced into the cavity onto the predetermined point on the substrate as liquid drops, with adjusting the relative position of the substrate fixed to said one tray and the sample discharge port, thereby forming spots of the sample on one substrate, removing said one tray from the first moving table, mounting another tray to which the other substrate is fixed on the first moving table, discharging each sample having been introduced into the cavity onto the predetermined point on the substrate as liquid drops, with adjusting the relative position of the other substrate and the sample discharge port, thereby forming spots of the sample on one substrate, and repeating the process a number of times equal to the number of the trays.

7. The biochip manufacturing method according to claim 2, which comprises, providing plural number of robots each of which is composed of said first moving table and second moving table, mounting tray on which the substrate is fixed on the first moving table forming one robot among said plural number of robots, discharging the sample provided to one discharge head mounted on said second moving table is d onto the predetermined point on the substrate as liquid drops, with adjusting the relative positions of the substrate and the sample discharge port, thereby forming spots of the sample provided to one discharge head on the substrate, removing said one tray, mounting the removed tray on one first moving table forming other robot among said plural number of robots, discharging the sample provided to the other discharge head on the one second moving table composing said other robot onto the predetermined point on the substrate as liquid drops, thereby forming spots of the sample on one substrate, and repeating the process a number of times equal to the number of the robots.

8. The biochip manufacturing method according to claim 7, wherein spots are formed on another substrate with said one robot using another tray on which said another substrate is fixed, during a period that spots are formed on said one substrate by using said another robot after forming spots on said one substrate using said one robot.

9. The biochip manufacturing method according to claim 2, which comprises, carrying at least one of two operations out, wherein one operation is measuring the position of said discharge head with respect to the absolute coordinates of said second moving table, which is performed each time the discharge head is mounted on the second moving table, and another operation is measuring the position of said tray with respect to the absolute coordinates of said first moving table, which is performed each time the tray is mounted on the fist moving table, calculating the relative positional relationship of the said discharge head and the said tray based on the measured results, and discharging the sample onto the predetermined point on the said substrate fixed on the said tray to form spots.

10. The biochip manufacturing method according to claim 9, wherein positional deviation of the discharge head and the tray is corrected by repeating the position measurement of the discharge head with respect to the absolute coordinates of the second moving table and the position measurement of the tray with respect to the absolute coordinates of the first moving table for an optional number of times.

11. The biochip manufacturing method according to claim 9, which comprises, providing the discharge head with head reference marks in at least two predetermined locations, providing the second moving table with second table fixing references at two or more locations of the immovable part thereof, measuring the relative positions of the head reference marks and the second table fixing references at two or more locations, and based on the measured results obtained, correcting the direction and amount of deviation of the mounting position of the head by decomposing the deviation in the longitudinal, lateral, and rotational directions.

12. The biochip manufacturing method according to claim 11, which comprises, providing the first moving table with the table reference marks at two or more locations on the movable part thereof and first table fixing reference marks at two or more locations on the immovable part thereof, measuring the relative positions of the head reference mark and the first table fixing references at two or more locations, providing the tray with the tray reference marks in at least two predetermined locations of the tray, measuring the relative positions of the tray reference marks and the first table fixing references at two or more locations, and correcting the direction and amount of deviation of the mounting position of the tray by decomposing the deviation in the longitudinal and lateral directions, based on the measured results obtained.

13. The biochip manufacturing method according to claim 2, wherein at least one of the first moving table and the second moving table is moved while correcting by using an outside reference fixed in the immovable part of at least one of the first moving table and the second moving table.

14. The biochip manufacturing method according to claim 13, wherein said outside reference is made from a material with a low thermal expansion coefficient.

15. The biochip manufacturing method according to claim 2, which comprises, moving the first moving table and the second moving table while adjusting the relative position of the substrate and the sample discharge port so that the discharge head and the tray are brought to predetermined positions, and discharging the sample from the sample discharge port to form spots in the state in which the discharge head and the tray are in stationary conditions.

16. The biochip manufacturing method according to claim 2, which comprises, providing a discharge head equipped with two or more discharge modules, providing a tray equipped with two or more substrates fixed thereon, moving the tray to have a predetermined positional relationship between the sample discharge ports of all discharge units in one discharge module and one substrate among the two or more substrates fixed on the tray, while simultaneously adjusting the relative positions of the sample discharge ports for all discharge units in one discharge module and one substrate among the two or more substrates fixed on the tray, discharging the sample having been stored in said one discharge module onto said one substrate from the sample discharge ports for all discharge units in said one discharge module, thereby forming spots corresponding to the sample discharge ports for all discharge units in said one discharge module, and, moving the tray to establish a predetermined positional relationship between said one substrate and the sample discharge ports of all discharge units in another discharge module, while simultaneously adjusting the relative positional relationship between the substrate and the sample discharge ports of all discharge units in said another discharge module, discharging the sample stored in said another discharge module onto said one substrate from the sample discharge ports for all discharge units in said another discharge module, thereby forming spots corresponding to the sample discharge ports for all discharge units in said another discharge module, repeating this process for a number of times equal to the number of discharge modules arranged in said discharge head, thereby forming spots on said one substrate corresponding to the sample discharge ports for all discharge units present in the discharge head, and moving the tray to secure another substrate on the tray, thereby forming spots corresponding to sample discharge ports for all discharge units present in the discharge head, repeating this process for a number of times equal to the number of substrates fixed on the tray, and with maintaining intervals of sample discharge operations from said discharge units in said two or more discharge modules almost the same.

17. The biochip manufacturing method according to claim 16, which comprises, discharging the sample having been stored in said one discharge module onto said one substrate from the sample discharge ports for all discharge units in said one discharge module, thereby forming spots, and moving the tray with the discharge head being in stationary conditions to establish a predetermined positional relationship between one substrate and the sample discharge ports of all discharge units in another discharge module, while simultaneously adjusting the relative positional relationship between the substrate and the sample discharge ports of all discharge units in said another discharge module, after forming spots on said one substrate corresponding to the sample discharge ports for all discharge units present in the discharge head, and moving the tray with the discharge head being in stationary conditions to establish a predetermined positional relationship between said another substrate and said sample discharge ports of all other discharge units in said another discharge module, while adjusting the relative positional relationship between the substrate and the sample discharge ports of all discharge units in said another discharge module.

18. The biochip manufacturing method according to claim 17, wherein the discharge head is vertically removed from the tray before moving the tray, and after moving the tray, the discharge head is vertically moved to approach the tray.

19. The biochip manufacturing method according to claim 2, wherein the sample is discharged from the discharge units at regular intervals merely for the purpose of dummy discharge during the time other than the period in which a series of operations for forming spots on predetermined points on substrates by discharging samples from the sample discharge ports are performed.

20. The biochip manufacturing method according to claim 19, wherein the intervals of the dummy discharge become almost the same as the intervals of the sample discharge, beginning from before the time when the series of operations is started for forming spots on predetermined points on substrates by discharging samples from the sample discharge ports.

21. The biochip manufacturing method according to claim 1, wherein the upper surface of the substrate is irradiated with a coaxial light after forming spots on predetermined points of the substrate by discharging the samples from said sample discharge ports, and a spot configuration is measured by the image produced by reflection of light on the surface of the substrate on which spots have been formed, thereby accumulating propriety information about the spots.

* * * * *